United States Patent [19]

Soreq

[11] Patent Number: 5,215,909

[45] Date of Patent: Jun. 1, 1993

[54] HUMAN CHOLINESTERASE GENES

[75] Inventor: Hermona Soreq, Rishon Le Zion, Israel

[73] Assignee: Yeda Research & Development Co., Ltd., Israel

[21] Appl. No.: 572,911

[22] Filed: Aug. 15, 1990

Related U.S. Application Data

[63] Continuation of Ser. No. 87,724, Aug. 21, 1987, abandoned, which is a continuation-in-part of Ser. No. 875,737, Jun. 18, 1986, abandoned.

[51] Int. Cl.$^5$ .......................... C12N 5/10; C12N 1/12; C12N 1/15; C12N 15/12
[52] U.S. Cl. ................................ 435/240.2; 435/172.3; 435/252.3; 435/254; 435/255; 435/320.1; 536/23.2
[58] Field of Search ................. 435/320.1, 69.1, 252.3, 435/172.3, 240.2, 254, 255; 536/27

[56] References Cited

PUBLICATIONS

Soreq et al. PNAS 82:1827–1831 (1985) Abstract.*
Soreq et al. Symp. Giovanni Lorenzin: Found. 20:95–9 (1984) Abstract only.
Prody et al. J. Neurosci; Res. 16:25–35 (1986) Abstract only.
Maniatis et al. Molecular Cloning C.S.H.L. 1982.
Doctor et al., Proc. Natl. Acad. Sci. USA 80:5767–5771 (1983).
Fambrough et al., Proc. Natl. Acad. Sci. USA 79:1078–1082 (1982).
Schumacher et al., Nature 319:407–409 (1986).
Soreq et al. Proc. Natl. Acad. Sci. USA 79:830–835 (1982).
Soreq et al., EMBO J. 3:1371–1375 (1984).
Soreq et al., In: Developmental Neuroscience (Caciagli et al. eds.) pp. 95–99 (1984).

Primary Examiner—Richard A. Schwartz
Assistant Examiner—J. LeGuyader
Attorney, Agent, or Firm—Sterne, Kessler, Goldstein & Fox

[57] ABSTRACT

This invention is directed to genetically engineered proteins having human ChE activity, and more particularly, the activity of human AChE or human pseudo-ChE. The invention also provides for DNA sequences encoding such proteins, and more specifically DNA sequences comprising the entire coding region for encoding such complete proteins, and DNA expression vectors comprising such sequences. The invention also provides for DNA, which as been joined outside living cells, capable of infecting culturable cells, to be maintained therein and in progenies thereof which is adapted to encode such active proteins. The invention further provides culturable cells infected with recombinant DNA defined above, and to purified proteins having human ChE activity produced by such cells. There are further provided antibodies interacting with human AChE and pseudo-ChE and assays based on the use of such antibodies. The invention also provides compositions counteracting the effects of succinylcholine and of organophosphorus, containing as active ingredient an effective dosage of proteins defined above.

7 Claims, 10 Drawing Sheets

HUMAN CHOLINESTERASE GENES

CROSS-REFERENCE TO RELATED APPLICATIONS

This application is a continuation of application Ser. No. 087,724, filed Aug. 21, 198, now abandoned, which is a continuation-in-part of U.S. patent application Ser. No. 875,737, filed Jun. 18, 1986, now abandoned the contents of which are fully incorporated herein by reference.

FIELD OF THE INVENTION

This invention relates to genetically engineered proteins having human cholinesterase activity, comprising either acetylcholinesterase activity or pseudocholinesterase activity. This invention is also directed to the cloning and production of these proteins. This invention further relates to using these proteins to produce antibodies interacting with human cholinesterase. The proteins of this invention can also be used in medical treatment of organophosphorus poisoning.

BACKGROUND OF THE INVENTION

Structural and Physiological Properties of Cholinesterases

At the cholinergic synapse, the enzyme acetylcholinesterase terminates the electrophysiological response to the neurotransmitter acetylcholine (ACh) by degrading it very rapidly. (For a review, see Silver, A., *The Biology of Cholinesterases.* North-Holland Pub. Co., Amsterdam (1974)). Mammalian cholinesterases (ChEs) exhibit extensive polymorphism at several levels. They can be distinguished by substrate specificity into acetylcholinesterase (acetylcholine hydrolase, EC 3.1.1.7, AChE) and butylcholinesterase or pseudocholinesterase (acylcholine acylhydrolase, EC 3.1.1.8, $\psi$ChE). These cholinesterases differ in their susceptibility to various inhibitors. Both are composed of subunits of about 600 amino acid residues each and are glycosylated (10–20%).

ChEs occur in multiple molecular forms, which exhibit different sedimentation coefficients on sucrose gradients, display different hydrodynamic interactions with non-ionic detergents and are composed of different numbers of subunits. (For a comprehensive review see Massoulie, J., and Bon, S., *Ann. Rev. Neurosci.* 5:57–106 (1982)). There are secreted, cytoplasmic, and membrane-associated pools of ChEs in the mammalian nervous tissue, but all forms of ChEs possess similar catalytic properties, suggesting that they share common acetylcholine binding sites (Chubb, I. W., In: *Cholinesterases—Fundamental and Applied Aspects.* M. Brzin, E. A. Barnard, and D. Sket, Eds., pp. 345–359, (1984)). Various ChEs may also contain distinct polypeptide regions, responsible for the subcellular segregation of various AChE forms, for their different amphipathic properties and for their different modes of assembly into multisubunit protein molecules. This is supported by the reports of antibodies which display homologies (Fambrough et al., *Proc. Natl. Acad. Sci. USA* 79:1078–1082 (1982)), as well as differences (Doctor et al., *Proc. Natl. Acad. Sci. USA* 80:5767–5771 (1983)) between different forms of AChE from various organisms.

Interaction of Cholinesterases with Organophosphorus Insecticides and Nerve Gases Most of the commonly used insecticides are organophosphorus (OP) compounds, acting by blocking the insect's AChE. In many cases where such insects develop insensitivity to the insecticides, this occurs because of the enhanced expression of AChE forms which do not interact with the organophosphate. To deal with such phenomenae successfully, it is necessary to know the mechanisms by which the appearance of such AChE forms is regulated.

Complete inhibition of mammalian AChE (i.e., by administration of OP-poisons) is lethal, due to the formation of a stable stoichiometric (1:1) covalent conjugate with the active site serine. Treatment of OP poisoning has involved the use of reversible ChE inhibitors, and reactivation of the inhibited enzyme with active-site directed nucleophiles (e.g., quaternary oximes) which detach the phosphoryl moiety from the hydroxyl group of the active site serine. A parallel competing reaction, termed "aging," transforms the inhibited ChE into a form that cannot be regenerated by the commonly used reactivators by dealkylation of the covalently bound OP group, and renders therapy of intoxication by certain organophosphates, such as Sarin, DFP, and Soman, exceedingly difficult (National Academy of Sciences Report, 1982).

Frequent Mutations in Cholinesterase Genes

Pseudocholinesterase ($\psi$ChE) is particularly enriched in the serum. Subjects with "null" $\psi$ChE activity (i.e., samples of their serum cannot hydrolyze acetylcholine) do not exhibit any health problem under natural conditions but suffer from prolonged apnea when they are given succinylcholine (a drug commonly used as a short-acting muscle relaxant) in surgical operation. However, there are no rapid, simple, routine methods to detect and characterize the atypic forms of the enzyme prior to surgery.

The amino acid sequence of human AChE is not known. It has recently been found that the same six amino acids are included in the organophosphorus binding site of both Torpedo AChE tetramers and human pseudoChE tetramers. (McPheeQuigley, K., *J. Biol. Chem.* 206:12185–12189 (1985); Schumacher et al., *Nature* 319:407–409 (1986)).

The amino acid sequence in this hexapeptide from the organophosphate-binding site of ChEs has been determined recently in several laboratories, by partial proteolytic digestion of the purified enzymes, labeled with [$^3$H]-diisopropylfluorophosphate, and was found to be Gly-Glu-Ser-Ala-Gly-Ala, with the serine residue bound to organophosphates. It has been suggested that the "null" forms of $\psi$ChE are modified in this peptide.

Common Alterations in the Level and Properties of Cholinesterases

Modifications in both the level (Spokes, E.G.S., Brain 103:179–183 (1980)) and the composition of molecular forms (Atack, J. R., et al., *Neurosci. Lett.* 40:199–204 1983)) of human brain AChE have been reported in several neurological or genetic disorders, such as Senile Dementia of the Alzheimer's type (SDAT; about 5% of the population above 65), or Down's syndrome (trisomy of chromosome 21). The levels of AChE in cholinergic brain areas drops by about 50%, and the tetrameric form of the enzyme disappears completely in SDAT. Individuals with Down's syndrome invariably develop SDAT manifestations before the age of 40. In addition, open neural tube defects in human embryos are clinically characterized by secretion of AChE tetramers into the amniotic fluid. Current tests for these phenomenae include sucrose gradient fractionation, followed by enzymatic assays of substrate hydrolysis or gel electrophoresis and AChE activity staining. Missing, and particularly desirable, are simple selective procedures to determine the level of specific AChE forms.

Homozygote Drosophila mutants lacking the Ace locus which controls AChE biosynthesis die at a very early stage of larval development (Hall, J. O., *Quar. Rev. Biophysics* 15:3-479 (1982)). Nematode mutants defective in the expression of one of their two cholinesterase genes cannot survive. It is highly likely that homozygous mutations in AChE genes in humans will result in early abortion or in severe neuromuscular malformations in the fetus. So far, there are no methods to determine whether specific individuals carry such mutations.

SUMMARY OF THE INVENTION

The invention is directed to the neurotransmitterhydrolyzing enzyme, acetylcholinesterase (AChE), which is a key element in cholinergic synapses and in neuromuscular junctions. It is also directed to the homologous and closely related enzyme butyrylcholinesterase or pseudocholinesterase ($\psi$ChE), abundant in the serum and present in muscle and brain synapses. Cholinesterases (ChEs) appear in different cell types, where they exist in multiple molecular forms. According to the invention, several types of cDNA and mRNA are provided which code for the main types of human ChE. Genetic engineering was used to provide sources for the large-scale production of various ChE types.

According to the invention, there is thus provided genetic sequences encoding a polypeptide or protein having human ChE activity. The invention also provides for expression vectors containing such genetic sequences, hosts transformed with the expression vectors, and methods for producing the genetically engineered or recombinant ChE polypeptide or protein.

The ChE peptides produced by the methods of this invention are useful in the treatment of organophosphorus poisoning (OP), as an antidote for the treatment of patients poisoned by such poisonous substances.

The ChE peptides produced by the methods of this invention can also be used to elicit antibodies raised against such peptides. These antibodies which specifically interact with human cholinesterase may be used for the detection of disease-related changes of ChEs in patients.

DETAILED DESCRIPTION OF THE INVENTION

Figure 1:
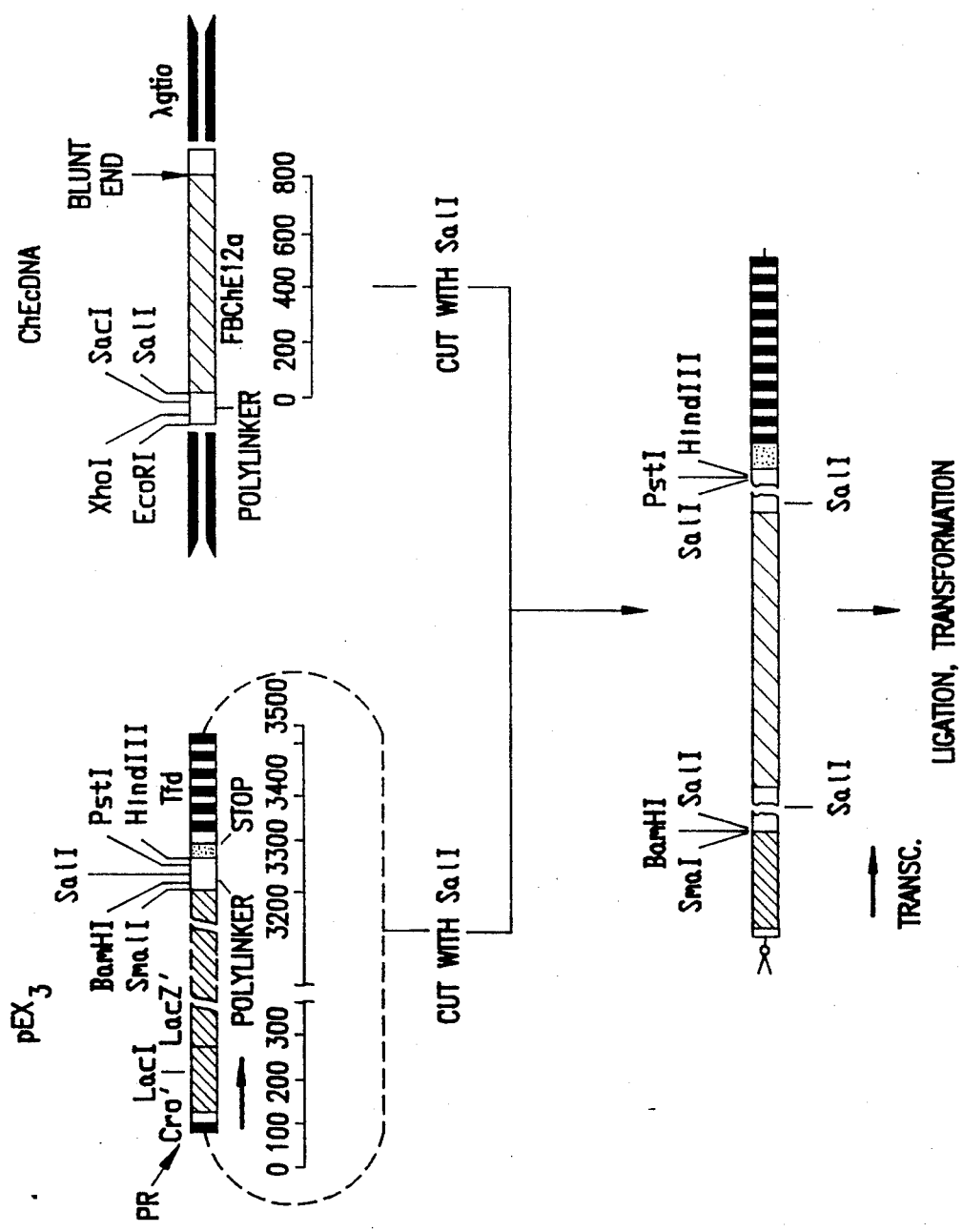
FIG. 1 shows the FBChE12 insert transcribed from $\psi$ChEmRNA and subcloned into the pEX3 expression vector to produce pEX3-FBChE12 plasmids.

The process for genetically engineering a protein having human ChE activity, such as human AChE or human pseudo-ChE activity, according to the invention, requires the cloning of the genetic sequences of the protein and expression of the DNA sequences.

The DNA sequences of the protein having ChE activity may be derived from a variety of sources. These sources include genomic DNA, cDNA, synthetic DNA, and combinations thereof. The genomic DNA may or may not include naturally occurring introns.

The DNA obtained from the genomic DNA or cDNA may be obtained in a variety of ways. Cells coding for the desired sequence may be isolated, the genomic DNA fragmented, conveniently by one or more restriction endonucleases, and the resulting fragments cloned and screened with a probe for the presence of the DNA sequence coding for ChE, AChE, or pseudo-ChE activity.

The joining of the various fragments is performed in accordance with conventional techniques, employing blunt-ended or staggered-ended termini for ligation, restriction enzyme digestion to provide for appropriate termini, filling in of cohesive ends as appropriate, alkaline phosphatase treatment to avoid undesirable joining, and ligation with appropriate ligases.

For cDNA, the cDNA may be cloned and the resulting clone screened with an appropriate probe for cDNA coding for the desired sequences. Once the desired clone has been isolated, the cDNA may be manipulated in substantially the same manner as the genomic DNA. However, with cDNA there will be no introns or intervening sequences.

Further, the genes of the protein having human ChE activity may be synthesized according to well-known means and cloned for use in preparing the active enzyme in large scale and in producing antibodies.

To express the protein, transcriptional and translational signals recognized by an appropriate host are necessary. Eukaryotic hosts will be mammalian cells capable of culture in vitro. Alternatively, non-mammalian cells may be employed, such as bacteria, fungi, e.g., yeast, filamentous fungi, or the like.

The DNA sequence coding for the protein may be obtained in association with the promoter region from genomic DNA. To the extent that the host cells recognize the transcriptional regulatory and translational initiation signals associated with the expression of the protein, then the region 5' of the protein coding sequence may be retained and employed for transcriptional and translational initiation regulation.

The contiguous non-coding region 5' to the protein coding sequence will normally include those sequences involved with initiation of transcription and translation, such as the TATA box, capping sequence, CAAT sequence, and the like. Usually the 5'-non-coding sequence will be at least 150 bp, more usually at least 200 bp, usually not exceeding about 2 kbp, more usually not exceeding about 1 kbp.

The non-coding region 3' to the genes coding for the protein may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

The construct, containing the sequences coding for the desired protein and the appropriate promoter and termination signals, may be introduced into a cell by transformation in conjunction with a gene allowing for selection where the construct will become integrated into a host genome. Usually the construct will be part of a vector having a replication system recognized by the host cell.

Expression vehicles for production of the proteins of the invention include plasmids or other vectors. In general, such vectors containing replicon and control sequences which are derived from species compatible with a host cell are used in connection with the host. The vector ordinarily carries a replicon site, as well as specific genes which are capable of providing phenotypic selection in transformed cells. For example, *E. coli* is readily transformed using pBR322, a plasmid derived from an *E. coli* species. pBR322 contains genes for ampicillin and tetracycline resistance, and thus provides easy means for identifying transformed cells. The pBR322 plasmid or other microbial plasmids must also contain, or be modified to contain, promoters which can be used by the microbial organism for expression of its own proteins. Those promoters most commonly used in recombinant DNA construction include the beta lactamase, lactose promoter systems, lambda phage promoters, and the tryptophan promoter systems. While these are the most commonly used, other microbial promoters have been discovered and can be utilized. These include, for example, the bacteriophage T7RNA polymerase/promoter system for the controlled exclusive expression of specific genes (S. Tabor and C. C. Richardson, PNAS 82:1074-1078 (1985)), a system in which the cloned protein may be induced to levels as high as 20% of total cellular protein.

For example, a genetic construct for the protein can be placed under the control of the leftward promoter of bacteriophage lambda. Control is exerted by the lambda repressor, and adjacent restriction sites are known.

The expression of the protein can also be placed under control of other regulatory sequences which may be homologous to the organism in its untransformed state. For example, lactose dependent *E. coli* chromosomal DNA comprises a lactose or lac operon which mediates lactose utilization by elaborating the enzyme beta-galactosidase. The lac control elements may be obtained from bacteriophage lambda lac5, which is infective for *E. coli*. The lac promoter-operator system can be induced by IPTG.

Other promoter/operator systems or portions thereof can be employed as well. For example, colicin E1, galactose, alkaline phosphatase, tryptophan, xylose, tax, and the like can be used.

Other hosts are mammalian cells, grown in vitro in tissue culture, or in vivo in animals. Mammalian cells provide post-translational modifications to protein molecules including correct folding or glycosylation at correct sites. Also, they may produce non-catalytic subunits that are required for the correct association of ChE with the cell membrane. Mammalian cells which may be useful as hosts include cells of fibroblast origin such as VERO or CHO-K1, or cells of lymphoid origin, such as the hydridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct p.t. processing.

For a mammalian host, several possible vector systems are available for the expression of the cholinesterase molecules. One class of vectors utilizes DNA elements which provide autonomously replicating extrachromosomal plasmids, derived from animal viruses such as bovine papilloma virus, polyoma virus, adenovirus, or SV40 virus. A second class of vectors relies upon the integration of the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotropic host, biocide resistance, e.g., antibiotics, or heavy metals, such as copper, or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Mol. Cel. Biol.* 3:280 (1983).

A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

Another preferred host is yeast. Yeast provides substantial advantages in that it can also carry out posttranslational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

Any of a series of yeast gene expression systems incorporating promoter and termination elements from the actively expressed genes coding for glycolytic enzymes produced in large quantities when yeast are grown in mediums rich in glucose can be utilized. Known glycolytic genes can also provide very efficient transcriptional control signals. For example, the promoter and terminator signals of the phosphoglycerate kinase gene can be utilized.

Once the vector or DNA sequence containing the construct(s) has been prepared for expression, the DNA construct(s) may be introduced into an appropriate host. Various techniques may be employed, such as protoplast fusion, calcium phosphate-precipitation, electrophoration, direct microinjection, or other conventional technique. After the fusion, the cells are grown in a selective medium, where untransformed cells are killed, leaving only cells transformed with the DNA construct. Expression of the gene(s) results in assembly to form the polypeptide or protein having ChE, AChE, or pseudo-ChE activity. This can take place in the transformed cells as such, or following the induction of these cells to differentiate (for example, by administration of bromodeoxyuracil to neuroblastoma cells or the like).

The expressed protein may be isolated and purified in accordance with conventional conditions, such as extraction, precipitation, chromatography, affinity chromatography, electrophoresis, or the like.

The present invention provides for means of producing ample quantities of the polypeptide or protein having ChE activity which binds to organophosphorus poisons with a very high Kd value. These recombinant polypeptides or proteins can be used in pharmaceutical compositions for use in the prophylaxis of, or for the treatment of, the effects of organophosphorus compound poisoning, which contains as an active ingredient a ChE type enzyme as described in this invention. The pharmaceutical composition may also contain a pharmaceutically acceptable carrier. These carriers are well known in the art and can include aqueous or solvent emulsions or suspensions, including saline and buffered media. The pharmaceutical art, for example, as described in *Remington's Pharmaceutical Sciences* (16th Edition, 1980).

Another utility of this invention is the clinical detection of $\psi$ChE deficiencies, which will prevent the post-surgery prolonged apnea phenomenon, using oligonucleotide hybridization to genomic DNA, similar to the detection of abnormalities in the gene coding for sickle cell beta-S globin (Corner et al., *Proc. Natl. Acad. Sci. USA* 80:278-282 (1983)). This invention provides for an assay adapted to distinguish between these normal and defective sequences in minute samples of genomic DNA and in a single hybridization step.

Further, the elucidation of the active site topography and the amino acid sequence of AChE opens up new approaches for the development of rapid, simple clinical methods to detect poisoning or disease-related changes in ChEs. This can be done, for example, by radioimmunoassay, using monospecific antibodies elicited against peptide domains that are specific to the tetrameric form, which appears to be the major one to be altered in various neurological disorders.

Finally, if indeed it will be proved that mutations in ChE gene(s) are lethal or cause severe damage, a method to detect such mutations at the level of DNA can be provided, which enables the defective genes to be identified at a very early gestational stage. This can be done by hybridization tests, using DNA from chronic villi or amniotic fibroblasts and well-characterized probes from ChE gene(s).

According to the invention, there is further provided an assay for the determination in mammals, including humans, genetically altered cholinesterase-producing genes. Details of this assay are set out in the following, such assay comprising essentially the following steps:

a. extracting DNA from cells of the patient;
b. effecting an enzymatic restriction of the DNA;
c. electrophoretically separating fragments of the DNA and blotting the fragments on a suitable support;
d. providing a labeled DNA or RNA probe of predetermined sequence from the polypeptides or proteins having ChE activity of this invention;
e. hybridizing such fragments of (c) with a probe of (d);
f. determining according to the hybridization pattern the presence or absence of such altered genes.

Having now generally described this invention, the same will become more readily understood by reference to specific examples included herein for purposes of illustration only, and are not intended to be limited unless otherwise specified.

EXAMPLE I

Identification of mRNA Species Coding for Human ChEs

To identify the mRNA species coding for human ChEs, the use of microinjected Xenopus oocytes was developed as a highly sensitive and efficient translation system which is capable of producing catalytically active ChEs (Soreq, H., et al., *Proc. Natl. Acad. Sci. USA* 79:830-835 (1982)).

Injection of mRNA from different ChE-expressing sources into these oocytes produces ChE activities (Soreq, H., et al., *EMBO Journal* 3:1371-1375 (1984)). This bioassay issued to directly monitor the levels of ChEmRNA in the corresponding tissue. In combination with our recently developed methods for measuring ChE activity (Parvari, R., et al., Anal. Biochem. 133:450-456 (1983), we can now determine these activities with a particularly high sensitivity and also define the biochemical properties of the oocyte-produced enzyme (see Soreq, H., *CRC Critical Reviews in Biochem.* Vol. 18, 199-238 (1985) for a recent review).

Determination of ChEmRNA levels in the oocytes was proven to be time- and concentration-dependent and the enzyme produced from brain poly(A)+RNA was biochemically defined as "true" mammalian AChE. When the concentration of ChEmRNA out of total poly(A)+RNA was calculated, it yielded values of about $1\times10^{-5}$ of total mRNA. (Soreq et al., ibid. (1984)).

Sucrose gradient fractionation of DMSO-denatured mRNA from primary gliomas, meningiomas and embryonic brain revealed three size classes of ChE-inducing mRNAs, sedimenting at 32S, 20S, and 9S. The amounts of these different classes of ChE-inducing mRNAs varied between the three tissue sources examined. To distinguish between ChEs produced in oocytes and having different substrate specificities, their activity was determined in the presence of selective inhibitors. Both AChE and $\psi$ChE multimeric cholinesterase activities were found in the mRNA-injected oocytes. Moreover, human brain mRNAs inducing "true" and "pseudo" ChE activities had different size distribution, indicating that different mRNAs might be translated into various types of ChEs. These findings imply that the heterogeneity of ChEs in the human nervous system is not limited to the post-translational level, but extends to the level of mRNA. Furthermore, the composition of ChEmRNAs appears to be different in various brain cell types, and the production of the differently migrating ChE molecular forms thus seems to be controlled at least partially at the level of mRNA.

To ensure a complete representation of all of the ChEmRNA sequences in different cell types in the brain, it was necessary to prepare the cDNA library from the entire brain. Therefore, we could not take advantage of the fact that particular brain regions are highly enriched with AChE. Our mRNA preparation of choice was, therefore, total, unfractionated poly(A)+ mRNA from human fetal brain. To focus on the particular DNA sequences which actually code for the ChE proteins, it was decided to search for probes of high specificity and selectivity. Such properties could be offered by synthetic short oligonucleotides, prepared according to amino acid sequence(s) that are unique to cholinesterases.

EXAMPLE II

Use of Oligodeoxyribonucleotides in Hybridization Reactions

Synthetic oligodeoxyribonucleotides have been shown to hybridize specifically to complementary DNA sequences (Wallace, R. B., et al., Nuc. Acids Res. 9:879-894 (1981)). Under appropriate hybridization conditions, only well basepaired oligonucleotide xDNA duplexes will form; duplexes containing mismatched base pairs will not be stable. This technique has been applied to the successful isolation of cDNAs coding for human beta$_2$ macroglobulin, for murine transplantation antigen, for human apolipoprotein and many others. The consensus hexapeptide sequence from the organophosphate-binding site of ChEs (designated OPSYN) is Phe-Gly-Glu-Ser-Ala-Gly. Because of the ambiguity in the genetic code, this peptide could be encoded by one out of 384 different oligonucleotides, as follows:

OPSYN oligonucleotides

Phe Gly Glu Ser Ala Gly
AAG CCN CTC AGN CGN CC
 A       T  TCA
              C (where N = A, C, G, or T).

Three mixtures of these oligodeoxynucleotides, each containing 128 different chains of 17 nucleotides each, designated OPSYN, were prepared by solid phase synthesis using phosphoramidite chemistry (Beaucage et al., Tetra. Lett. 22:1859-1862 (1981); Mcbride et al., Tetra. Lett. 24:245-248 (1983); Atkinson et al., Oligonucleotide Synthesis—A Practical Approach, Gate, M. J. (ed.), IRL Press, 35-81 (1984)). The synthetic procedure employed was essentially that given by Adams et al., J. Am. Chem. Soc. 105:661-663 (1983). In synthetic cycles where mixtures of two or four nucleotides had to be introduced, the solid support was divided into two or four equal parts. Each of the portions was reacted with only one of the required phosphoramidite reagents. Following this cycle, the various portions were recombined. This procedure ensured the presence, in the mixture, of roughly equal amounts of each of its components. The oligodeoxynucleotides were purified by polyacrylamide gel electrophoresis (20% acrylamide, 7M urea), followed by Sephadex G-50 chromatography.

The OPSYN probes are rich in guanosine and cytosine residues. The hybridization with these probes was carried out at 40° C., to prevent high non-specific binding. Phage DNA was transferred from plaques to nitrocellulose filters (Maniatis et al., Molecular Cloning, A Laboratory Manual. Cold Spring Harbor Laboratory Press (1982)). Filters were incubated for prehybridization in 6×SSC (1×SSC=0.015M sodium citrate and 0.15M NaCl), 5×Denhardt (1×Denhardt's solution is 0.02% Ficoll/0.02% polyvinylpyrollidone/0.02% bovine serum albumin) and 0.1 mg/ml salmon sperm DNA for 2 h at 40° C. This step was followed by hybridization in 6×SSC, 5×Denhardt, 0.05 mg/ml salmon sperm DNA and 3×10$^6$ dpm/ml of [$^{32}$P]-labeled oligonucleotide probe, for 16 h at 40° C. Filters were then washed at 40° C. in 3×SSC, 40 min each wash with 4-8 changes of washing solution until released radioactivity decreased below 300 dpm/ml. Exposure duration was 1-3 days with intensifying screens (CAWO) (2-3 days for first screen, 1 day for further screens). Following the third screening step, 3M tetramethylammonium chloride ((CH$_3$)$_4$NCl) was employed to discriminate against short, GC-rich hybrids in a base composition-independent manner (Wood et al., Proc. Natl. Acad. Sci. USA 82:1585-1588 (1985)). Filters were first rinsed at 37° C. with 3M (CH$_3$)$_4$NCl solution, containing 50 mM Tris HCl, pH 8.0, 2 mM EDTA and sodium dodecyl sulfate at 1 mg/ml. Rinsed filters were washed twice in a shaking bath for 20 min with the same (CH$_3$)$_4$NCl solution at 53° C.±1° C.

To increase the certainty of our search, we prepared an additional oligodeoxynucleotide probe. This probe, designated OPSYNO, consisted of a mixture of 36 oligodeoxynucleotides, each 29 nucleotides long. These encoded a decapeptide comprising the same hexapeptide as the OPSYN probes and four additional amino acids, Ala-Ala-Ser-Val, as reported for the continuation of this peptide in human serum ψChE (Lockeridge, O., "Cholinesterases--Fundamental and Applied Aspects," edited Brzin et al., pp. 5-12 (1984)). To limit the complexity of this probe and ensure that the correct oligodeoxynucleotide would be present in sufficient specific activity, we inserted deoxyiosine in every position where all four nucleotides might be found. Deoxyinosine, being an "inert" nucleotide, is expected either to hybridize with A, C, or T or at least not to interfere with the stability of hybridization (Takahashi et al., Proc. Natl. Acad. Sci. USA 82:1931-1933 (1985)). However, the stability of such non-perfect hybrids, containing deoxyinosine, is expected to be lower than that of perfect hybrids of the same length (Takahashi, ibid. (1985)). This implies that to remain stable under our washing conditions, OPSYNO×cDNA hybrids should contain more than 17 base pair matches. In other words, OPSYN-positives with 16-17 base pair matches that do not represent the correct cDNA can be excluded with the aid of OPSYNO.

EXAMPLE III

Isolated cDNA Clone. Designated FBChE12

A. Description of FBChE12

Altogether, four screening experiments were performed; these resulted in the isolation of 8 $(CH_3)_4NCl$-stable clones, out of which only one hybridized with OPSYNO as well. Furthermore, the hybridization signals displayed by this clone with both OPSYN I and II and OPSYNO were the only ones that remained stable to 3M $(CH_3)_4NCl$ washes. The isolated cDNA insert, designated FBChE12, consisted of 765 nucleotides with an open reading frame sufficient to code for about half of the subunit size of human cholinesterase (Lockridge, ibid. (1984)).

The nucleopeptide sequence of FBChE12 that is complementary to probes OPSYN and OPSYNO corresponded exactly to the peptide sequence used to design these oligodeoxynucleotide probes. When the amino acids predicted from FBChE12 sequence are aligned with the available peptide sequences published for human ψChE, about half of the coding region for the mature enzyme is defined, starting at residue 1 (nucleotide 187), which corresponds to the N-terminal peptide, and ending at residue 202, which is included in the active site tryptic peptide of ψChE as determined from amino acid sequencing. The sequence includes the active site serine, which can be labeled by diisopropylfluorophosphate (Lockbridge, ibid. (1984)). The N-terminal peptide inferred by the FBChE12 sequence is similar to the ψChE peptide, except that in our sequence residue 12 is Lys, as in the N-terminal peptide of Torpedo AChE (McPhee-Quigley et al., ibid. (1985)), whereas the corresponding residue of human ψChE found by amino acid sequencing is Gly. In addition, the N-terminus of the ChE encoded by FBChE12 differs from the peptide reported for erythrocyte AChE (Haas and Rosenberry, *Anal. Biochem.* 148:154-162 (1985)). Altogether, this suggests that FBChE12 codes for ψChE.

The region upstream of the ψChE amino-terminal residue (nucleotides 115-187) in FBChE12 codes for 20 amino acids characteristic of leader peptides of membrane-associated and exported protein precursors. The hydrophobic sequence in this region is rich in large nonpolar amino acids. It is preceded by the tripeptide His-Ser-Lys, and terminates with Lys-Ser-His, both composed of polar amino acids. Further upstream, the cDNA sequence consists of a fully open reading frame without stop codons and includes two methionine residues. The DNA and inferred amino acid sequence of the FBChE12 clone were compared to the parallel sequences recently published for a cDNA clone coding for AChE from Torpedo electric organ (Schumacher et al., ibid. (1986)). This analysis revealed a 47% homology between the corresponding parts of the Torpedo and the human enzymes, strongly suggesting that they have a common ancestral origin. A higher level of conservation was found at the amino acid level than at the DNA level. For direct characterization of the protein encoded by FBChE12, the cDNA insert was subcloned into the pEX bacterial expression vector in conjunction with the gene coding for β-galactosidase.

B. Expression of a Partial ψChEcDNA Clone in a Bacterial Plasmid

In order to search for the similarities and differences between various ChEs at the level of the naked polypeptide, the FBChE12 insert transcribed from ψChEmRNA was subcloned into the pEX bacterial expression vector. For this purpose, the polylinker oligonucleotide which was used to construct the fetal brain cDNA library in gt10 was restricted with the enzyme SalI and the cDNA insert thus produced was religated at the 3'-end of the gene coding for β-galactosidase in the pEX plasmid linearized with SalI.

FIG. 1 shows the construction of pEX3-FBChE12 plasmids. In FIG. 1, the synthetic oligodeoxynucleotide polylinker employed to construct the fetal brain and liver cDNA libraries in gt10 DNA is presented. It contains four restriction sites for the enzymes SalI, SacI, XhoI and EcoRI, with the latter serving as an attachment site to the gt10 DNA, whereas the insert is blunt-end ligated with the other end of the polylinker oligodeoxynucleotide. Thus, each of these enzymes may serve to excise the cDNA insert from the gt10 vector.

The FBChE12 cDNA insert was excised from the gt10 vector by SalI restriction and subcloned into the SalI site of the pEX polylinker oligodeoxynucleotide. There are three types of the pEX vectors, adjusted for insertion of cDNA fragments in three reading frames.

Figure 2:
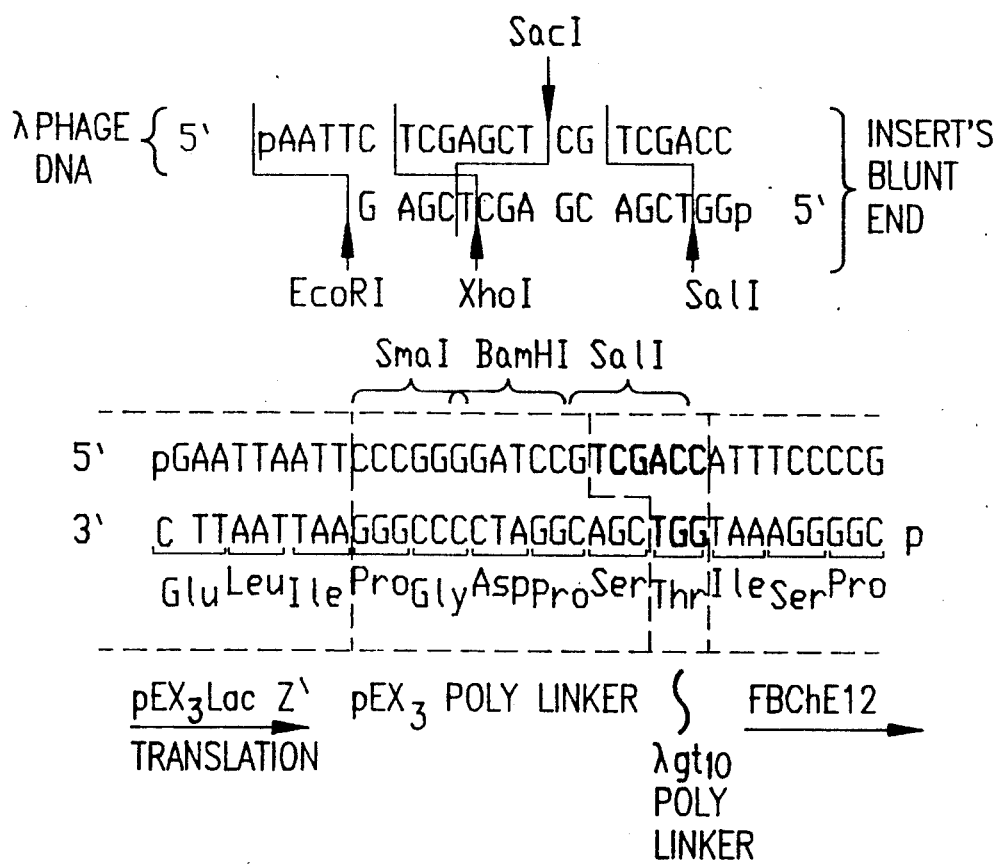
FIG. 2 shows the oligodeoxynucleoptide sequence in the ligation region between the pEX3LacZ' gene and the FBChE12 cDNA insert.

FIG. 2 shows the oligodeoxynucleotide fragment linking between the LacZ' gene of the pEX3 vector and the 5'-region of the FBChE12 cDNA insert. The resultant construct contained, in an open reading frame, parts from the polylinker regions employed to construct the pEX3 vector (thin letters) and the gt10 library (bold letters). The direction of translation is marked by an arrow and restriction sites included in the oligodeoxynucleotide construct are noted.

Sequence analysis of the FBChE12 clone indicated that the FBChE12 cDNA insert should contain a SalI site in the same reading frame as pEX3. However, ligation could occur in both orientations and thus only ca. 50% of the transformed bacterial colonies obtained with pEX3FBChE12 constructs were expected to enable correct translation of the cDNA insert, leading to production of a fusion protein with β-galactosidase.

The recombinant pEX3 FBChE12 plasmids were amplified in *E. coli* POP2136 bacteria at 30° C. up to the density of $1 \times 10^8$ cells/ml, with β-galactosidase synthesis blocked by the temperature-sensitive cIts857 repressor. Transient expression of β-galactosidase fusion protein was induced by shifting to 42° C. for one hour and bacteria were harvested by centrifugation. Proteins were extracted from the pellet of bacteria carrying pEX3FBChE12 recombinants (+) or native pEX3 plasmids (−) by vigorous agitation for 15 minutes at 37° C. in 1 ml of 35 mM Tris-HCl buffer pH 7.4 containing o.67% Triton X-100, 0.67M NaCl, 67 mM dithiothreitol, and 7% $NaDodSO_4$ for a 60 ml culture. One volume of 0.2M Tris HCl buffer, pH 6.8, containing 20% glycerol, 6% β-mercaptoethanol, and 0.01% bromophenol blue was then added and the mixture was boiled for 10 minutes. Ten ul samples of this mixture were subjected to protein gel electrophoresis for 3 hours and 100 V in 0.5 mm thick gradient slab gels (5-15% polyacrylamide). Protein bands that were found by staining to be enhanced in bacteria infected with FBChE12-pEX recombinants (Fraction 1, approx. 70-75 kd, and 2, approx. 30-40 kd) were purified and concentrated by preparative gel electrophoresis, electroelution, and lyophilization. The size of the induced protein was examined by SDS-polyacrylamide gel electrophoresis. Bacterial cultures, in which β-galactosidase ceased to be expressed in its native form under these conditions, were used for further analysis.

Under normal conditions, shift to 42° C. of the bacteria transformed with pEX plasmids results in the induction of synthesis of β-galactosidase. In contrast, induction of β-galactosidase expression in bacteria transformed with the pEX-ψChE constructs resulted in the production of a fusion protein of ca. 125 kd in length, which was mostly proteolyzed in the bacteria to yield a series of proteolytic products in the range of 35,000-75,000 daltons. It should be noted in this respect that the fusion proteins produced from cDNA inserts of greater than 400 nucleotides in pEX vectors tend to be proteolyzed in the bacteria. On the other hand, the synthesis of intact β-galactosidase (110 kd) ceased in these bacteria, as compared with its synthesis in bacteria transfected with the original pEX plasmid.

Figure 3:
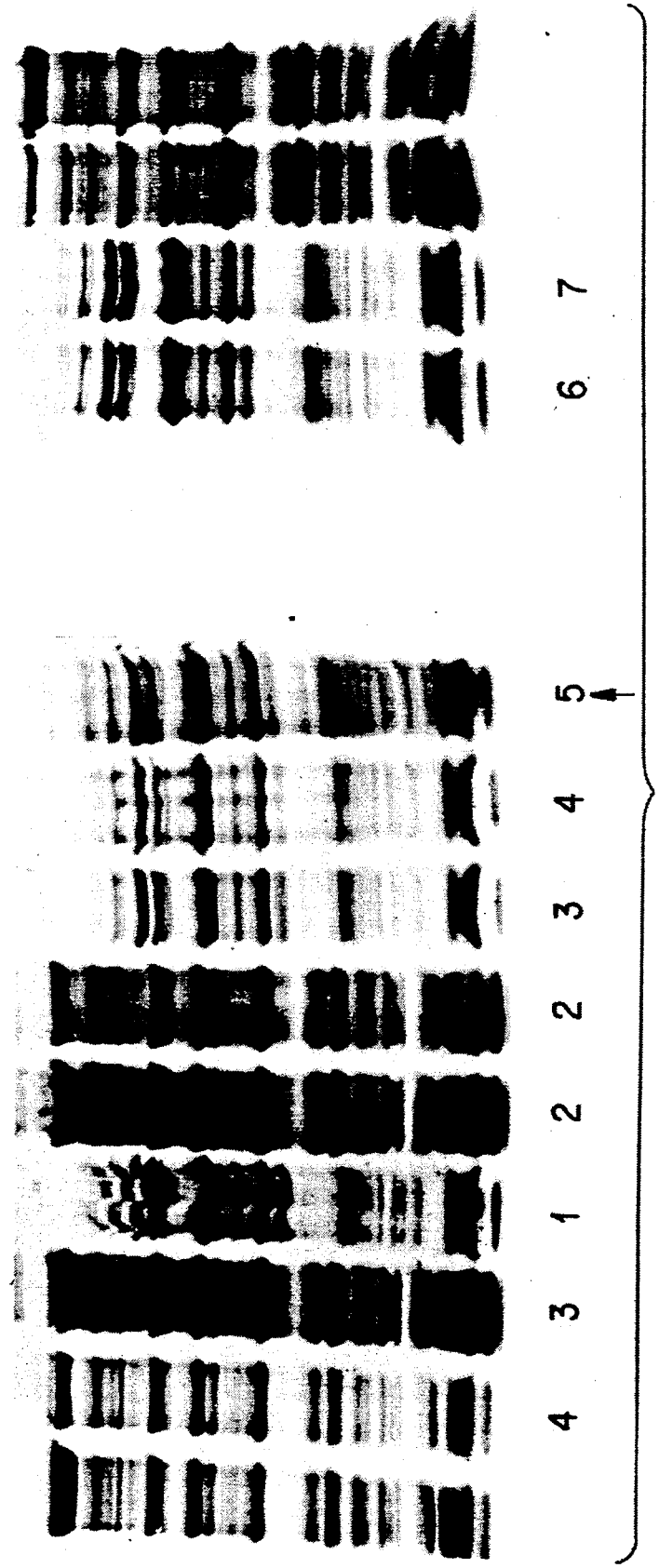
FIG. 3 shows the expression of FBChE12 in the pEX bacterial vector.

The proteins extracted from recombinant (+) or native (−) pEX3 plasmids and proteins purified from fractions 1 and 2 (see FIG. 3) were electrophoresed. Proteins were blotted onto nitrocellulose filters by overnight electroelution at a 50 mA constant current in a buffer containing 20 mM Trisma base, 150 mM glycine, 20% methanol, and 0.05% NaDodSO$_4$, at pH 8.3. Nitrocellulose blots were agitated for 30 minutes at 37° C. in a PBS-milk mixture, containing phosphate buffered saline and 5% non-fat dry milk powder (Cadbury). Filters were incubated in first antibody solution by shaking in PBS-milk, all with agitation at room temperature, using 200 ml per wash. The second antibody (F(ab)$_2$) fragment of donkey anti-rabbit IgG, conjugated to horseradish peroxidase (Amersham) and diluted 1:50 in PBS-milk) was added for 90 minutes with agitation at room temperature. Filters were then washed as before, rinsed for 2 minutes in 100 mM TrisHCl pH 7.6, prewarmed to 37° C., and incubated in staining solution (3 mg/ml 3-amino-9-ethylcarbazol (Aldrich) in N,N-dimethylformamide, mixed prior to staining with 100 volumes of 50 mM NaAcetate pH 5.0 containing 0.015% H$_2$O$_2$). Staining developed in a few minutes at room temperature, and filters were rinsed in water, air-dried, and photographed. The rabbit antisera employed were against bacterial β-galactosidase (gratefully received from Dr. Ruth Arnon, the Weizmann Institute), human erythrocyte AChE (gratefully received from Dr. Urs Brodbeck, Switzerland), and Torpedo electric organ AChE (gratefully received from Dr. Palmer Taylor, San Diego), and were all used at a final dilution of 1:1000.

Antiserum against the fragment of human ψChE expressed in pEX3FBChE12 plasmids was prepared and purified as detailed above. It was then used for immunoblot analysis in 1:500 dilution. Proteins were extracted from the pellets of bacteria carrying pEX3FBChE12 recombinants (+) or native pEX3 plasmids (−), and highly purified human erythrocyte AChE (20 ng, gratefully received from Dr. T. August, Baltimore) were loaded in parallel.

Figure 4:
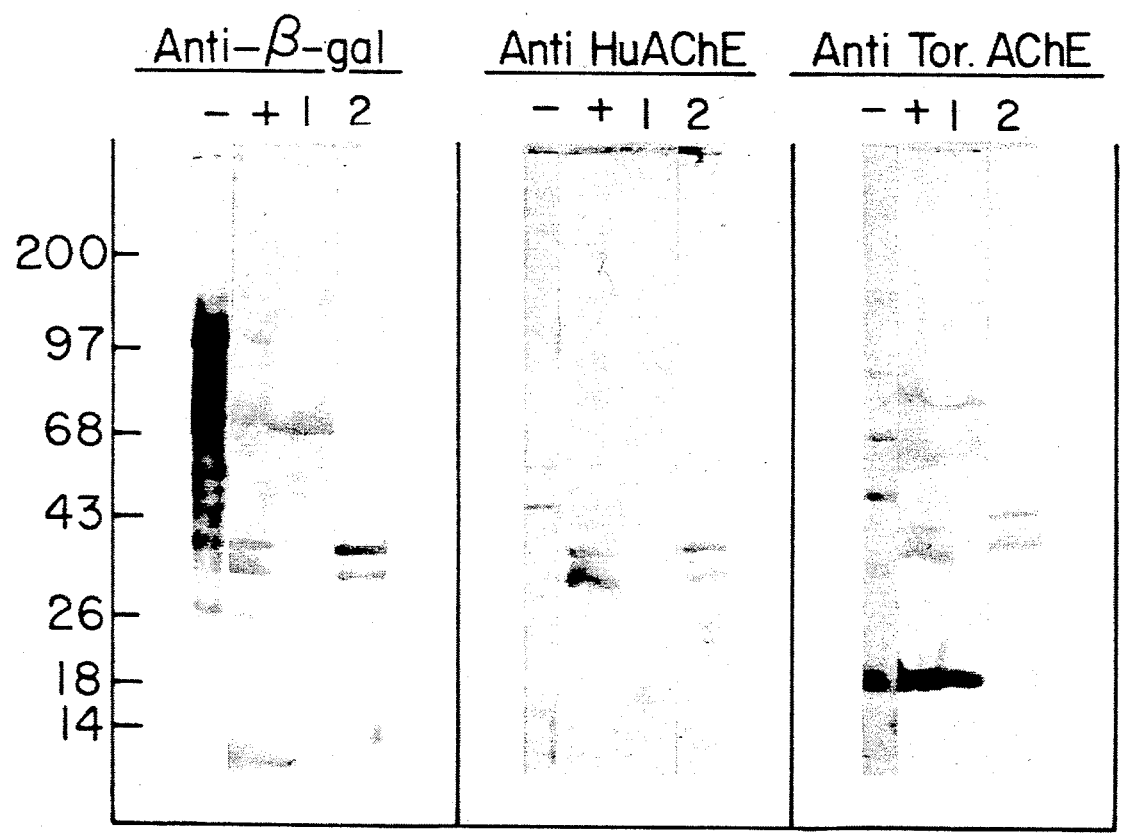
FIG. 4 shows the reactivity of proteins expressed in pEX3PBChE12 with antibodies against bacterial $\beta$-galactosidase and human and Torpedo acetylcholinesterase.

The nature of the polypeptides translated from pEX-ψChE plasmids was examined by immunoblot analysis of bacterial extracts. It was found that all of the peptides produced from the fusion protein reacted with antibodies against bacterial β-galactosidase, and that the 40 kd and 35 kd peptides, but not the other ones, interacted specifically in protein blots with rabbit antibodies against both human erythrocyte and Torpedo electric organ AChE (FIG. 4). In addition, the 40 kd and 35 kd polypeptides reacted specifically in immunoblots with all of the AEI-$_{1-5}$ mouse monoclonal antibodies raised against human erythrocyte AChE. Altogether, this confirmed that these polypeptides are derived from a partially proteolyzed fusion protein of β-galactosidase-FBChE12, with the 40 kd and 35 kd polypeptides containing the information encoded by the FBChE12 cDNA insert. Furthermore, the immunoblot analysis revealed that this ψChE-derived polypeptide shares immunological properties with both human and Torpedo AChE. Protein blot analysis with antiserum against whole human serum proteins failed to reveal a significant specific interaction, perhaps because the antibodies interacting with ψChE in this complex antiserum could only recognize the mature protein.

C. Anti-cholinesterase Antibodies Elicited against the Protein Product of ψChEcDNA as Synthesized in Bacteria The bacterial-produced ψChE-derived peptide is available in a naked, nonmodified form. Antibodies elicited against this polypeptide should, in principle, be mostly directed against primary sequence epitopes of human pseudocholinesterase and may reveal sequence homologies and differences between ChEs of various forms and species.

Figure 5:
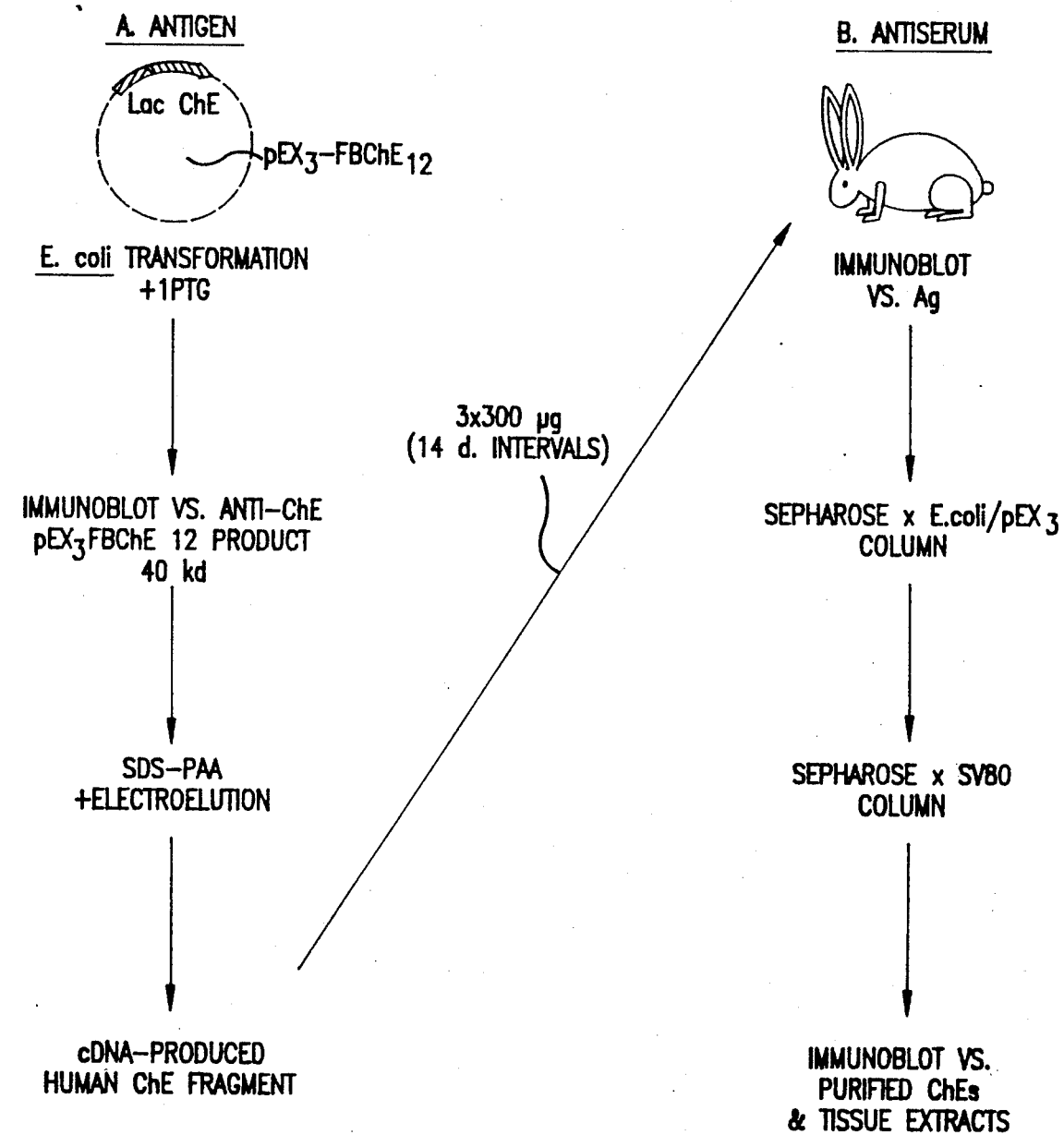
FIG. 5 shows the scheme for the elicitation and purification of rabbit antiserum against the protein product of human $\psi$ChE cDNA.

For these reasons, we have used the 40 kd and 35 kd protein products synthesized in bacteria from the FBChE12 insert to elicit rabbit anti-ChE antibodies. First, this protein was purified by polyacrylamide gel electrophoresis and electroelution. It was then injected into rabbits in 300 ug quantities together with Freund's complete adjuvant, three times at 14-day intervals. The resultant rabbit serum was tested by immunoblot analysis against the electrophoretically purified antigen and purified by affinity chromatography on two successive Sepharose 4B columns as follow: protein extracts from E. coli bacteria transformed with pEX3 plasmids alone (without cDNA inserts) and protein extracts from SV80 human fibroblasts, which express no ChE activites whatsoever, were covalently bound to two Sepharose preparations, respectively. The affinity chromatography of the antiserum on these columns resulted in the removal of antibodies directed against both irrelevant bacterial proteins and cross-reactive irrelevant human proteins. The general procedure for the elicitation and purification of the anti-cloned ψChE anti-serum is schematically drawn in FIG. 5.

Figure 6:
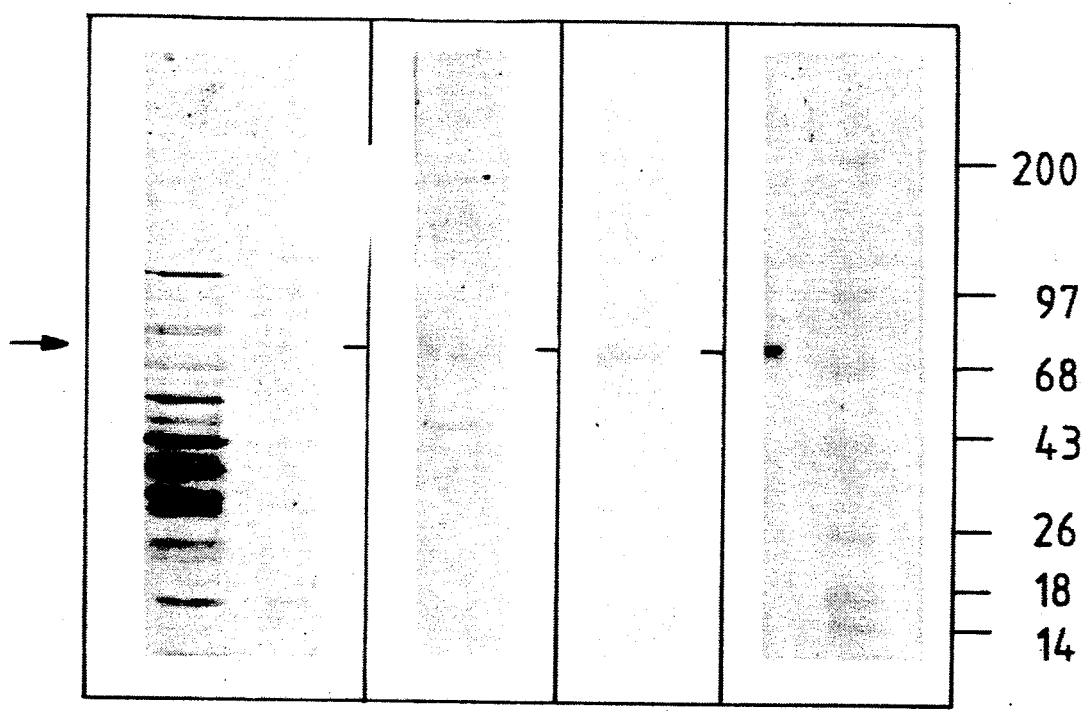
FIG. 6 shows the immunoblot analysis with antibodies elicited against a cloned fragment of human $\psi$ChE.

The anti-cloned ChE antiserum purified as above was tested by immunoblot analysis with purified human erythrocyte AChE, as well as with non-purified human serum and with proteins extracted from fetal human muscle, from E. coli bacteria transformed with pEX3 non-recombinant plasmids and from bacteria transformed with pEX3×FBChE12 plasmids. The results are shown in FIG. 6. The antiserum reacted specifically with a polypeptide of the size of 70,000 kd in all three preparations of human proteins and with a set of polypeptides the largest of which was greater than 95,000 kd in the pEX3×PBChE12-transformed bacteria. This analysis demonstrated that the anti-cloned ψChE antiserum interacts specifically with highly purified erythrocyte AChE and with a similarly migrating protein in human serum and muscle.

Induction of pEX expression resulted in the production of two polypeptides, of 90 and 40 kilodalton, which reacted with anti β-galactosidase antibodies, while the synthesis of intact β-galactosidase (117 kilodalton) ceased almost completely. The 40 kd polypeptide, but not the 90 kd one, interacted specifically in protein blots with antibodies against both human erythrocyte and Torpedo electric organ AChE, suggesting that both polypeptides are derived from a partially proteolyzed fusion protein of β-galactosidase-FBChE12, with the 40 kd polypeptide containing the information encoded by FBChE12. Protein blot analysis with anti-serum against whole human serum proteins failed to reveal a significant specific interaction (not shown), perhaps due to the low amount of anti-cholinesterase antibodies in this polyspecific antiserum.

EXAMPLE IV

Materials and Methods

A. Construction of SP6-cholinesterase Vector

The full-length cDNA coding for human ψChE was inserted into the pSP64 vector (Promega-Biotec) immediately downstream from the Salmonella bacteriophage promoter. The experimental strategy used is schematically displayed as follows and in FIG. 7:

1. The pSP64 vector (Promega-Biotec) was linearized by restriction with the enzyme SmaI with the M13 polylinker region (M) introduced into this vector.
2. The fetal liver ψChEcDNA gt10 clone, containing an insert of 2450 nucleotides in length, was digested by EcoRI, thus producing gt10 "arms" and two fragments of the ψChE DNA insert: a 2250 base-pair fragment (FLψChEcDNA) which contained most of the cDNA sequence, and a 190 nucleotides long fragment from the 5'-terminal domain coding for the N-terminal part of the ψChE protein. The FLψChEcDNA was isolated by preparative gel electrophoresis and electroelution.
3. The cohesive ends produced in this fragment by EcoRI restriction were repaired using the Klenow subunit of DNA polymerase and the resultant cDNA fragment was blunt-end ligated into the SmaI site of the linearized pSP64 vector. E. coli bacteria were transformed with the ligated pSP64-FL constructs and colonies containing recombinant plasmids were detected by agarose gel electrophoresis of whole colony extract DNA. In order to select plasmids into which the insert was introduced in a correct orientation as referred to the SP6 promoter, plasmid DNA was prepared from about 10 of these colonies. Restriction of plasmid DNA by BamHI produced a fragment of 580 base pairs only in cases where the insert was introduced in the correct orientation.
4. To prepare for completion of the cDNA insert, the pSP64-FL plasmid DNA was linearized by restriction with SalI and then cut with AccI. This removed part of the polylinker region and exposed an AccI site at a position 27 base pairs downstream from the 5'-end of the FLChE DNA.
5. The fetal brain FBChE12 clone was employed to prepare the region coding for the N-terminal domain of ψChE. Insert DNA was first excised with SalI and then restricted with AccI to yield a 275 basepair fragment with the appropriate enzyme site for insertion into the restricted pSP64-FL constructs. This fragment was purified by preparative gel electrophoresis and elecroelution.
6. The SalI-AccI fragment of FBChE12 was ligated into the SalI-AcI cut pSP64-ψChE plasmid, thus constructing the pSP64-ψChE plasmid containing fulllength ψChEcDNA introduced in the correct orientation for in vitro transcription.

B. In vitro Transcription and Translation of SP6ψChEmRNA

1. In vitro transcription and capping of pSP64-ψChE constructs was as follows: Briefly, the reaction mixture contained 40 mM Tris-HCl, pH 7.5, 6 mM $MgCl_2$, 2 mM Spermidine, 0.01% BSA, 10 mM Dithiothreitol, 0.5 mM of ATP, CTP, UTP, and GTP, 0.05 mM of $m^7GpppG$ (Pharmacia), 1 ug/ml of pSP64-ψChE DNA, unit/ul of human placental RNase Inhibitor (Amersham) and 0.2 units/ul of SP6 RNA polymerase (Promega-Biotech). Incubation was at 37° C. for 1.5 hours after which a second equal portion of RNA polymerase was added for an additional 1.5 hours. Reaction was stopped by adding DPRF grade DNAse (Worthington) to the final concentration of 2 units/ul for 20 minutes at 37° C. RNA was extracted twice by phenol:chloroform:isoamyl alcohol and once with chloroform: isoamyl alcohol. RNA was ethanolprecipitated, and RNA pellet was collected by 10 minutes centrifugation in an Eppendorf centrifuge, washed with 70% ethanol and dissolved in sterile, double-distilled water. Yields, as calculated by $A_{260}$ absorbance values (where 1 $A_{260}=40$ ug of RNA) were ca. 40 ug RNA from 10 ug of pSP64-ψChE template. Agarose gel electrophoresis of the ethidium-bromide strained RNA indicated that it mostly consisted of full-length, 2500 nucleotides long RNA chains.
2. Translation in vitro of the synthetic ψChEmRNA was performed in nuclease-treated reticulocyte lysate in the presence of [$^{35}$S]-methionine and translation products were analyzed by gradient SDS-polyacrylamide gel electrophoresis and autoradiography, in comparison with prelabeled molecular weight markers (BRL).

C. In ovo translation of synthetic ψChEmRNA into Catalytically Active Cholinesterase with High Sensitivity towards the ψChE-specific Organophosphate Inhibitor isoOMPA Synthetic ψChEmRNA was injected into Xenopus oocytes in 5 ng/oocyte quantities. Oocytes incubated for 20 hours at 18° C., incubation medium was separated, and oocytes were homogenized and fractionated into cytoplasmic and membraneextracted fractions. 10 ul samples from each fraction were incubated for 20 hours at room temperature with [$^3$H]-labeled acetylcholine with or without $10^{-5}M$ of the specific inhibitors iso-OMPA and BW284C51 and released [$^3$H]-acetate measured. 50 ng samples of poly A+ RNA from fetal brain were injected in parallel and water-injected oocytes served as control. Cholinesterase activities were calculated as nmol acetate released per hour by 1 ug of injected RNA, and spontaneous release of [$H^3$]-acetate was subtracted.

D. Expression of SP6ψChE Transcript in vitro and in ovo

In order to examine which of the properties characteristic of particular ChE forms are inherent to the primary mRNA sequence and which are added by post-translational processing, the full length cDNA coding for human ψChE was inserted into the $SP_6$ transcription vector and pure synthetic ψChEmRNA, prepared in vitro from these constructs, was examined by translation in vitro, in the nuclease treated reticulocyte lysate and in ovo, in microinjected Xenopus oocytes. In the reticulocyte lysate, this synthetic ψChEmRNA produced an [$^{35}$S]-methionine-labeled 69 kd polypeptide Thus, the SP$_6$mRNA microinjection experiments define necessary domains within the ChE molecule.

TABLE A

| | | Rough microinjection data-cpm/μl (20 hr incubation) | | | | | | | | |
|---|---|---|---|---|---|---|---|---|---|---|
| | | Medium | | | Cytoplasm | | | Extract | | |
| | | T | io | BW | T | io | BW | T | io | BW |
| Sp$_6$ΨChEmRNA | 1. | 12154 | 9071 | 8974 | 22861 | 17559 | 16705 | 9382 | 10431 | 11292 |
| | 2. | 13698 | 6841 | 11193 | 36988 | 5769 | 30211 | 18761 | 12305 | 19350 |
| | 3. | 17046 | 6270 | 11297 | 24493 | 7495 | 21366 | 14819 | 6470 | 16073 |
| | 4. | 15737 | 7407 | 14034 | 20722 | 7274 | 15494 | 13840 | 6897 | 16858 |
| Liver PA$^+$ | 1. | | | | | | | | | |
| | 2. | 7124 | 6726 | 5451 | 4690 | 7491 | 6904 | 6231 | 7298 | 5026 |
| | 3. | 6309 | 5627 | 6068 | 7049 | 7396 | 5815 | 7170 | 5924 | 5827 |
| Brain PA$^+$ | 1. | | | | | | | | | |
| | 2. | 6806 | 6254 | 6654 | 11175 | 9126 | 6269 | 6701 | 6729 | 6587 |
| | 3. | 10736 | 7245 | 5865 | 7411 | 8044 | 5857 | 5994 | 7932 | 7057 |
| Muscle PA$^+$ | 1. | 17610 | 10819 | 8998 | 11610 | 10610 | 6117 | 8541 | 6373 | 6127 |
| | 2. | 7065 | 6502 | 6471 | 5931 | 6555 | 6062 | 6768 | 6398 | 5894 |
| | 3. | 7983 | 6242 | 5816 | 7579 | 7043 | 5666 | 5977 | 6362 | 6437 |
| Liver + SP$_6$ | 1. | | | | | | | | | |
| | 2. | 9735 | 6997 | 7953 | 9090 | 8071 | 9887 | 6613 | 8481 | 4387 |
| | 3. | | | | | | | | | |
| Brain + SP$_6$ | 1. | | | | | | | | | |
| | 2. | 11925 | 8278 | 6669 | 9353 | 8789 | 5490 | 6219 | 6563 | 7497 |
| | 3. | | | | | | | | | |
| Muscle + SP$_6$ | 1. | 14233 | 11704 | 7491 | 11269 | 11802 | 11307 | 8451 | 6373 | 6127 |
| | 2. | 16760 | 13406 | 17234 | 28412 | 21024 | 30095 | 13089 | 10665 | 17850 |
| | 3. | | | | | | | | | |
| Barth | 1. | 6106 | 11957 | 8965 | 11084 | 7224 | 13112 | 8732 | 6531 | 4613 |
| (control) | 2. | 6350 | 5141 | 4729 | 6573 | 7201 | 7048 | 7558 | 6856 | 6223 |
| | 3. | 6804 | 6881 | 7417 | 9304 | 7995 | 6702 | 5923 | 6761 | 7077 |
| | 4. | 8097 | 10297 | 6505 | 6934 | 7937 | 5824 | 7057 | 4896 | 5803 |
| H$_2$O (bg) | 1. | 5690 | 7465 | 8266 | | | | | | |
| | 2. | 7303 | 8183 | 7142 | 6481 | 7394 | 7879 | | | |
| | 3. | 6450 | 6534 | 8230 | | | | | | |
| Eel (total) | 1. | *74045 | | | | | | | | |
| | 2. | 38234 | | | 52709 = 100 nmol | | | | | |
| | 3. | 45847 | | | | | | | | |

TABLE IB

| | ChE activities produced in microinjected Xenopus oocytes (nmol AChE/hr/μg RNA) | | | | | | | | |
|---|---|---|---|---|---|---|---|---|---|
| | Medium | | | Cytoplasm | | | Extract | | |
| Injected mRNA | T | io | BW | T | io | BW | T | io | BW |
| SP$_6$ΨChEmRNA | 155 | <0.1 | 66.3 | 375 | 40.4 | 248 | 146.4 | 31.2 | 128.4 |
| SP$_6$ + Liver PA$^+$ | 123 | <0.1 | 2.8 | 99 | 25.6 | 76.2 | 5.0 | 41.2 | <0.1 |
| SP$_6$+ Brain PA$^+$ | 206 | 33.5 | <0.1 | 109 | 52.9 | <0.1 | <0.1 | <0.1 | <0.1 |
| SP$_6$ + Muscle PA$^+$ | 342 | 195.9 | 188.6 | 472 | 342.3 | 487 | 162.8 | 24.3 | 156 |

Figure 7:
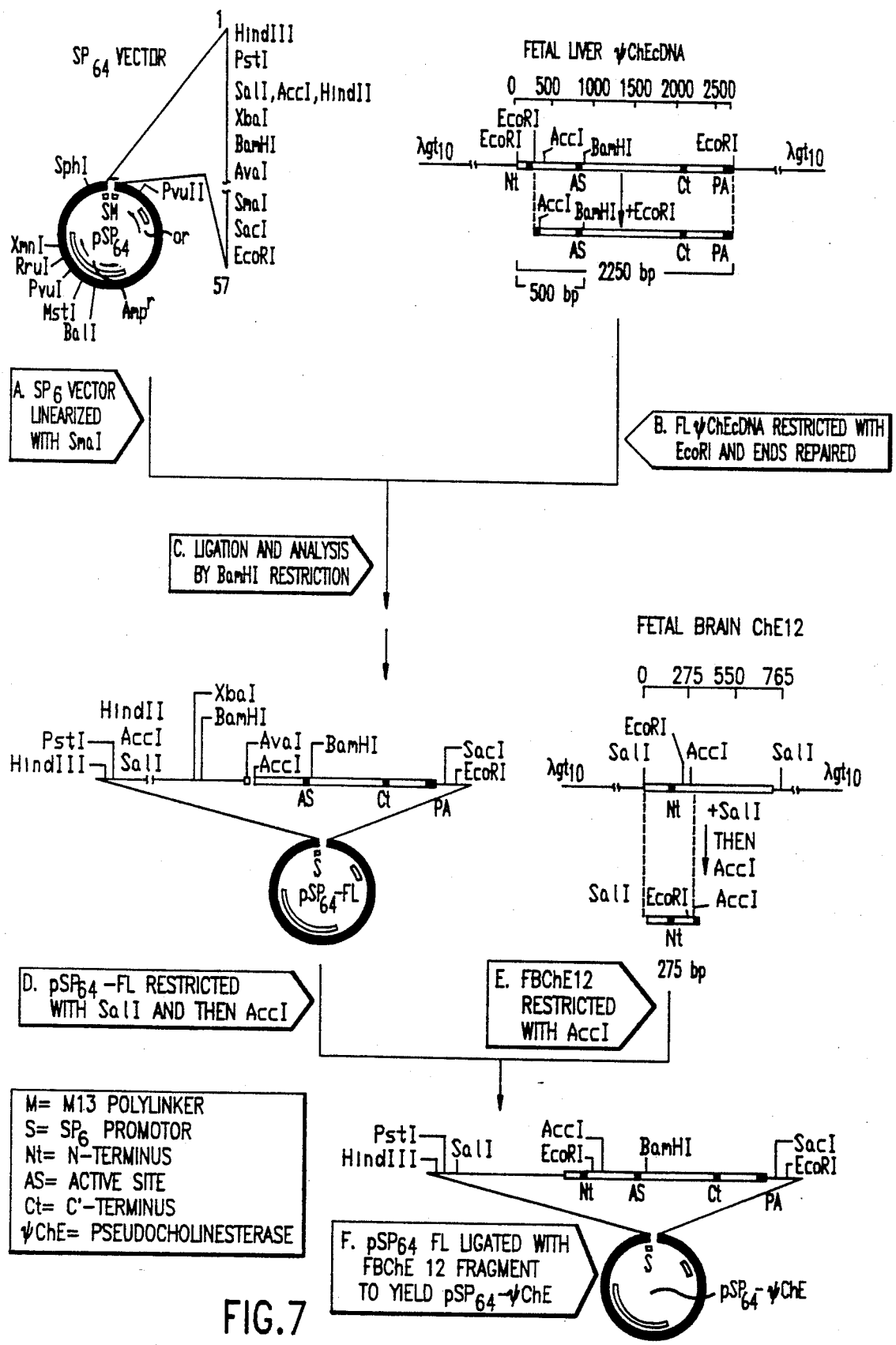
FIG. 7 shows the construction of the SP6-cholinesterase vector.

Activities are expressed in nmoles acetate released from $^3$H-acetylcholine per hour incubation per 1 μg of injected RNA.

with a rather low efficiency (FIG. 7). In microinjected oocytes, it was translated into catalytically active secretory cholinesterase with high sensitivity towards the ψChEspecific organophosphate inhibitor, iso-OMPA. The results of this study are shown in the following Tables A and B.

These experiments were confirmed and extended by activity measurements using the spectrophotometric assay of Ellman et al. (1962). Briefly, it was found that the synthetic ChEmRNA directed, with high efficiency, the production of catalytically active cholinesterase which segregated between the cytoplasm, medium and membrane fractions in the microinjected oocytes. The secreted activity displayed sensitivity to both iso-OMPA and BW284C51, suggesting that it behaves like both ψChE and AChE. In the membrane fraction, active dimers were detected by sucrose gradient fractionation with sedimentation coefficient of about 6.5 S. It was further determined that the poly(A) tail is essential to the stability of the ChEmRNA and that following the removal of the part coding for the c'-terminal 200 amino acids, the ChEmRNA still induces the production of enzyme with acetylcholine hydrolyzing activity.

Discussion

The purpose of this part of the study was to characterize the expression products of human ψChEcDNA clones as synthesized in bacterial cells and in microinjected Xenopus oocytes. The analyzed ψChEcDNA products displayed catalytic acetylcholine-hydrolyzing activity, assembly of subunits and sensitivity to selective ChE inhibitors. Several properties distinguish the nascent polypeptides translated from ψChEcDNA sequences from the various mature forms of human ChEs. When compared with the known properties of fully processed ChEs from different tissue sources, these analyses suggest strongly that the substrate-specificity properties of human ψChEs mostly stem from distinct domains in the primary amino acid sequence. Sensitivity to selective inhibitors, in contrast, appears to be specific to defined ChE forms and may arise from form-specific sequence domains with the additional contribution of distinct post-translational processing events.

Oocyte-microinjection experiments, as well as ChEmRNA translation in vitro, suggest that the polymorphism of cholinesterases extends to the level of mRNA. Homologous nonidentical mRNAs may be translated into various forms of ChEs, with distinct biochemical properties. Post-translational processing events such as cleavage of a signal peptide, glycosylation, intersubunit s-s bond formation, or covalent attachment of phosphatidylinositol may add to this polymorphism in a cell-type specific manner. Since no post-translational processing occurs in the in vitro translation system, one may expect the cDNA-derived ChE polypeptide produced in vitro to display properties of the naked ψChE polypeptide only, and differ from mature ChEs in its biochemical characteristics.

Our findings demonstrate that the pure synthetic ψChEmRNA is by itself sufficient to encode the synthesis of iso-OMPA sensitive ChE in microinjected Xenopus oocytes. This strongly suggests that the sensitivity to this selective organophosphorus inhibitor is inherent to the primary sequence of this particular ChEmRNA sequence. However, this conclusion should not be generalized for other ChE inhibitors. For example, the secreted ChE produced in oocytes from the $SP_6$ ψChEmRNA transcripts displays partial sensitivity to the AChE specific quaternary inhibitor BW284C51. This indicates that in contrast with iso-OMPA, the sensitivity to BW284C51 may be a property added to the nascent enzyme by post-translational processing events.

EXAMPLE V

In Vivo Biosynthesis of the Protein Encoded by FBChE12

To study the in vivo biosynthesis of the protein encoded by FBChE12, the inserted cDNA was [$^{32}$P]-labeled and hybridized with human RNA and DNA. In RNA blots loaded with 10 ug of poly(A)+RNA/lane, [$^{32}$P]-labeled FBChE12 interacted with a single 2.4 kb band of RNA that was present in fetal brain and liver but not in the cholinesterase-deficient Human Epidomoid carcinoma. The exposure time needed to visualize the hybridization was relatively long (10 days), suggesting that this mRNA exists at rather low concentrations even in positive tissue sources such a fetal brain and liver. This assumption was also corroborated by rescreening the fetal brain library with [$^{32}$P]-labeled FBChE12. Six out of $1 \times 10^6$ phages contained three different inserts that hybridized with FBChE12. Two of these were partial fragments included in FBChE12 and the third displayed only partial sequence homology with the original cDNA clone. This analysis emphasizes the scarcity of cholinesterase cDNA clones in the cDNA library. Further dot-blot experiments using poly(A)+RNA from several tissue sources proved that ChEmRNA levels are equally low. This demonstrates the high quality of the cDNA libraries employed, which included these rare sequences in spite of their very low concentration.

EXAMPLE VI mRNA Levels of Different Types of ChEs

The levels of the mRNAs coding for particular types of cholinesterase in fetal brain and liver were analyzed in parallel by mRNA microinjection into Xenopus oocytes, where AChEmRNA and ψChEmRNA are translated to yield their catalytically active enzyme products. Considerable production of iso-OMPA-insensitive AChE was observed in oocytes injected with either fetal brain of liver RNA but not with HEpRNA. In contrast, only liver mRNA was capable of producing significant levels of BW284C51-insensitive ψChE. Thus, the pattern revealed in the RNA blot hybridization is compatible with the levels of AChEmRNA, or with both species of cholinesterase mRNA together, but not with pseudo-ChEmRNA alone.

EXAMPLE VII

The Genomic Origin of FBChE12

The genomic DNA origin of FBChE12 was examined by DNA blot hybridization. [$^{32}$P]-labeled FBChE12 hybridized with two human DNA fragments derived by restriction with EcoRI, 4.7 and 2.5 kb in length. Taking into account the existence of an internal EcoRI site in the original FBChE12 cDNA clone, and comparing the signal intensity observed with 20 ug of genomic DNA to that detected with 1.0 ng of gt10-FBChE12, this analysis indicates that the DNA sequences hybridizing with FBChE12 are not present in the human genome in many copies. Parallel analysis of mouse DNA revealed a significant but not intense hybridization, suggesting the existence of homologous cholinesterase DNA sequences in other mammalian species. Accordingly, there is also provided a clone designated as FBChE12 which has the translated cDNA, amino acid sequence:

| ATT | TCC | CCG | AAG | TAT | TAC | ATG | ATT | TTC | ACT | CCT | 33 |
|-----|-----|-----|-----|-----|-----|-----|-----|-----|-----|-----|-----|
| Ile | Ser | Pro | Lys | Tyr | Tyr | Met | Ile | Phe | Thr | Pro | |

| TGC | AAA | CTT | TGC | CAT | CTT | TGT | TGC | AGA | GAA | TCG | 66 |
|-----|-----|-----|-----|-----|-----|-----|-----|-----|-----|-----|-----|
| Cys | Lys | Leu | Cys | His | Leu | Cys | Cys | Arg | Glu | Ser | |

| GAA | ATC | AAT | ATG | CAT | AGC | AAA | GTC | ACA | ATC | ATA | 99 |
|-----|-----|-----|-----|-----|-----|-----|-----|-----|-----|-----|-----|
| Glu | Ile | Asn | Met | His | Ser | Lys | Val | Thr | Ile | Ile | |

| TGC | ATC | AGA | TTT | CTC | TTT | TGG | TTT | CTT | TTG | CTC | 132 |
|-----|-----|-----|-----|-----|-----|-----|-----|-----|-----|-----|-----|
| Cys | Ile | Arg | Phe | Leu | Phe | Trp | Phe | Leu | Leu | Leu | |

| TGC | ATG | CTT | ATT | GGG | AAG | TCA | CAT | ACT | GAA | GAT | 165 |
|-----|-----|-----|-----|-----|-----|-----|-----|-----|-----|-----|-----|
| Cys | Met | Leu | Ile | Gly | Lys | Ser | His | Thr | Glu | Asp | |

| GAC | ATC | ATA | ATT | GCA | ACA | AAG | AAT | GGA | AAA | GTC | 198 |
|-----|-----|-----|-----|-----|-----|-----|-----|-----|-----|-----|-----|
| Asp | Ile | Ile | Ile | Ala | Thr | Lys | Asn | Gly | Lys | Val | |

| AGA | GGG | ATG | AAC | TTG | ACA | GTT | TTT | GGT | GGC | ACG | 231 |
|-----|-----|-----|-----|-----|-----|-----|-----|-----|-----|-----|-----|
| Arg | Gly | Met | Asn | Leu | Thr | Val | Phe | Gly | Gly | Thr | |

-continued

```
GTA ACA GCC TTT CTT GGA ATT CCC TAT GCA CAG      264
Val Thr Ala Phe Leu Gly Ile Pro Tyr Ala Gln

CCA CCT CTT GGT AGA CTT CGA TTC ACA AAG CCA      297
Pro Pro Leu Gly Arg Leu Arg Phe Thr Lys Pro

CAG TCT CTG ACC AGG TGG TCT GAT ATT TGG ACT      330
Gln Ala Thr Lys Tyr Ala Asn Ser Cys Cys Gln

GCC ACA AAA TAT GCA AAT TCT TGC TGT CAG AAC      363
Ser Leu Thr Arg Trp Ser Asp Ile Trp Thr Asn

ATA GAT CAT AGT TTT CCA GGC TTC CAT GGA TCA      396
Ile Asp His Ser Phe Pro Gly Phe His Gly Ser

GAG ATG TGG AAC CCA AAC ACT GAC CTC AGT GAA      429
Glu Met Trp Asn Pro Asn Thr Asp Leu Ser Glu

GAC TGT TTA TAT CTA AAT GTA TGG ATT CCA GCA      462
Asp Cys Leu Tyr Leu Asn Val Trp Ile Pro Ala

CCT AAA CCA AAA AAT GCC ACT GTA TTG ATA TGG      495
Pro Lys Pro Lys Asn Ala Thr Val Leu Ile Trp

ATT TAT GGT GGT GGT TTT CAA ACT GGA ACA TCA      528
Ile Tyr Gly Gly Gly Phe Gln Thr Gly Thr Ser

TCT TTA CAT GTT TAT GAT GGC AAG TTT CTG GCT      561
Ser Leu His Val Tyr Asp Gly Lys Phe Leu Ala

CGG GTT GAA AGA GTT ATT GTA GTG TCA ATG AAC      594
Arg Val Glu Arg Val Ile Val Val Ser Met Asn

TAT AGG GTG GGT GCC CTA GGA TTC TTA GCT TTG      627
Tyr Arg Val Gly Ala Leu Gly Phe Leu Ala Leu

CCA GGA AAT CCT GAG GCT CCA GGG AAC ATG GGT      660
Pro Gly Asn Pro Glu Ala Pro Gly Asn Met Gly

TTA TTT GAT CAA CAG TTG GCT CTT CAG TGG GTT      693
Leu Phe Asp Gln Gln Leu Ala Leu Gln Trp Val

CAA AAA AAT ATA GCA GCC TTT GGT GCA AAT CCT      726
Gln Lys Asn Ile Ala Ala Phe Gly Gly Asn Pro

AAA AGT GTA ACT CTC TTT GGA GAA AGT GCA GGA      759
Lys Ser Val Thr Leu Phe Gly Glu Ser Ala Gly

GCA GC                                            765
Ala Ala
```

EXAMPLE VIII

FBChE12 Clone Used as a Probe

The FBChE12 clone was further employed as a probe, to search for similar sequences in cDNA libraries derived from other tissue origins. Several such clones were thus isolated from a fetal liver cDNA library and from a primary glioblastoma cDNA library, cloned in gt10 phages. The fulllength sequence of the fetal human cholinesterase was deduced from these clones, as presented in the following ChE cDNA, amino acid sequence:

```
                                                                30                                                  60
CCG TCG ACC CCT GCA TTT CCC CGA AGT ATT TCC CCG AAC TAT TAC ATG ATT TTC ACT CCT
Pro Ser Thr Pro Ala Phe Pro Arg Ser Ile Ser Pro Asn Tyr Tyr Met Ile Phe Thr Pro 90                                                 120
TGC AAA GTT TGC CAT CTT TGT TGC AGA GAA TCG GAA ATC AAT ATG CAT AGC AAA GTC ACA
Cys Lys Val Cys His Leu Cys Cys Arg Glu Ser Glu Ile Asn Met His Ser Lys Val Thr 150                                                 180
ATC ATA TGC ATC AGA TTT CTC TTT TGG TTT GTT TTG CTC TGC ATG CTT ATT GGG AAG TCA
Ile Ile Cys Ile Arg Phe Leu Phe Trp Phe Val Leu Leu Cys Met Leu Ile Gly Lys Ser 210                                                 240
CAT ACT GAA GAT GAC ATC ATA ATT GCA ACA AAG AAT GGA AAA GTC AGA GGG ATG AAC TTG
His Thr Glu Asp Asp Ile Ile Ile Ala Thr Lys Asn Gly Lys Val Arg Gly Met Asn Leu
```

```
                                  270                                                        300
ACA GTT TTT GGT GGC ACG GTA ACA GCC TTT CTT GGA ATT CCC TAT GCA CAG CCA CCT CTT
Thr Val Phe Gly Gly Thr Val Thr Ala Phe Leu Gly Ile Pro Tyr Ala Gln Pro Pro Leu 330                                                        360
GGT AGA CTT CGA TTC ACA AAG CCA CAG TCT CTG ACC AGG TGG TCT GAT ATT TGG ACT GCC
Gly Arg Leu Arg Phe Thr Lys Pro Gln Ser Leu Thr Arg Trp Ser Asp Ile Trp Thr Ala 390                                                        420
ACA AAA TAT GCA AAT TCT TGC TGT CAG AAC ATA GAT CAT AGT TTT CCA GGC TTC CAT GGA
Thr Lys Tyr Ala Asn Ser Cys Cys Gln Asn Ile Asp His Ser Phe Pro Gly Phe His Gly 450                                                        480
TCA GAG ATG TGG AAC CCA AAC ACT GAC CTC AGT GAA GAC TGT TTA TAT CTA AAT GTA TGG
Ser Glu Met Trp Asn Pro Asn Thr Asp Leu Ser Glu Asp Cys Leu Tyr Leu Asn Val Trp 510                                                        540
ATT CCA GCA CCT AAA CCA AAA AAT GCC ACT GTA TTG ATA TGG ATT TAT GGT GGT GGT TTT
Ile Pro Ala Pro Lys Pro Lys Asn Ala Thr Val Leu Ile Trp Ile Tyr Gly Gly Gly Phe 570                                                        600
CAA ACT GGA ACA TCA TCT TTA CAT GTT TAT GAT GGC AAG TTT CTG GCT CGG GTT GAA AGA
Gln Thr Gly Thr Ser Ser Leu His Val Tyr Asn Gly Cys Phe Leu Ala Arg Val Glu Arg 630                                                        660
GTT ATT GTA GTG TCA ATG AAC TAT AGG GTG GGT GCC CTA GGA TTC TTA GCT TTG CCA GGA
Val Ile Val Val Ser Met Asn Tyr Arg Val Gly Ala Leu Gly Phe Leu Ala Leu Pro Gly 690                                                        720
AAT CCT GAG GCT CCA GGG AAC ATG GGT TTA TTT GAT CAA CAG TTG GCT CTT CAG TGG GTT
Asn Pro Glu Ala Pro Gly Asn Met Gly Leu Phe Asp Gln Gln Leu Ala Leu Gln Trp Val 750                                                        780
CAA AAA AAT ATA GCA GCC TTT GGT GGA AAT CCT AAA AGT GTA ACT CTC TTT GGA GAA AGT
Gln Lys Asn Ile Ala Ala Phe Gly Gly Asn Pro Lys Ser Val Thr Leu Phe Gly Glu Ser 810                                                        840
GCA GGA GCA GCT TCA GTT AGC CTG CAT TTG CTT TCT CCT GGA AGC CAT TCA TTG TTC ACC
Ala Gly Ala Ala Ser Val Ser Leu His Leu Leu Ser Pro Gly Ser His Ser Leu Phe Thr 870                                                        900
AGA GCC ATT CTG CAA AGT GGA TCC TTT AAT GCT CCT TGG GCG GTA ACA TCT CTT TAT GAA
Arg Ala Ile Leu Gln Ser Gly Ser Phe Asn Ala Pro Trp Ala Val Thr Ser Leu Tyr Glu 930                                                        960
GCT AGG AAC AGA ACG TTG AAC TTA GCT AAA TTG ACT GGT TGC TCT AGA GAG AAT GAG ACT
Ala Arg Asn Arg Thr Leu Asn Leu Ala Lys Leu Thr Gly Cys Ser Arg Glu Asn Glu Thr 990                                                        1020
GAA ATA ATC AAG TGT CTT AGA AAT AAA GAT CCC CAA GAA ATT CTT CTG AAT GAA GCA TTT
Glu Ile Ile Lys Cys Leu Arg Asn Lys Asp Pro Gln Glu Ile Leu Leu Asn Glu Ala Phe 1050                                                       1080
GTT GTC CCC TAT GGG ACT CCT TTG TCA GTA AAC TTT GGT CCG ACC GTG GAT GGT GAT TTT
Val Val Pro Tyr Gly Thr Pro Leu Ser Val Asn Phe Gly Pro Thr Val Asp Gly Asp Phe 1110                                                       1140
CTC ACT GAC ATG CCA GAC ATA TTA CTT GAA CTT GGA CAA TTT AAA AAA ACC CAG ATT TTG
Leu Thr Asp Met Pro Asp Ile Leu Leu Glu Leu Gly Gln Phe Lys Lys Thr Gln Ile Leu 1170                                                       1200
GTG GGT GTT AAT AAA GAT GAA GGG ACA GCT TTT TTA GTC TAT GGT GCT CCT GGC TTC AGC
Val Gly Val Asn Lys Asp Glu Gly Thr Ala Phe Leu Val Tyr Gly Ala Pro Gly Phe Ser 1230                                                       1260
AAA GAT AAC ATT AGT ATC ATA ACT AGA AAA GAA TTT CAA GAA GGT TTA AAA ATA TTT TTT
Lys Asp Asn Ile Ser Ile Ile Thr Arg Lys Glu Phe Gln Glu Gly Leu Lys Ile Phe Phe 1290                                                       1320
CCA GGA GTG AGT GAG TTT GGA AAG GAA TCC ATC CTT TTT CAA TAC ACA GAC TGG GTA GAT
Pro Gly Val Ser Glu Phe Gly Lys Glu Ser Ile Leu Phe Gln Tyr Thr Asp Trp Val Asp
```

-continued

```
                    1350                                                    1380
GAT CAA AGA CCT GAA AAC TAC CGT GAG GCC TTG GGT TGT ATG TTG TTG GGG ATT ATA ATT
Asp Gln Arg Pro Glu Asn Tyr Arg Glu Ala Leu Gly Cys Met Leu Leu Gly Ile Ile Ile 1410                                                    1410
TCA TAT GCC CTG CCG TTT GAA GTT ACC AAG AAG TTT TCA GAA TGG GGA AAT AAT GCC TTT
Ser Tyr Ala Leu Pro Phe Glu Val Thr Lys Lys Phe Ser Glu Trp Gly Asn Asn Ala Phe 1470                                                    1500
TTC TAC TAT TTT GAA CAC CGA TCC TCC AAA CTT CCG TGG CCA GAA TGG ATG GGA GTG ATG
Phe Tyr Tyr Phe Glu His Arg Ser Ser Lys Leu Pro Trp Pro Glu Trp Met Gly Val Met 1530                                                    1560
CAT GGC TAT AAA TTG AAT TTG TCT TTG GTT TAC CTC TGG AAA GAA GAG ATA ATT ACA CAA
His Gly Tyr Lys Leu Asn Leu Ser Leu Val Tyr Leu Trp Lys Glu Glu Ile Ile Thr Gln 1590                                                    1620
AAT CCT ATT AAA TTT AAG TAC ATC CAT AGT AAA CGG TGG GCA AAT TTT GCA AAA TAT GGG
Asn Pro Ile Lys Phe Lys Tyr Ile His Ser Lys Arg Trp Ala Asn Phe Ala Lys Tyr Gly 1650                                                    1680
AAT CCA AAT GAG ACT CAG ACC ATT AGC ACA AGC TGG CCT GTC TTA AAA GCA CTG AAC AAA
Asn Pro Asn Glu Thr Gln Thr Ile Ser Thr Ser Trp Pro Val Leu Lys Ala Leu Asn Lys 1710                                                    1740
ATA TCT AAC CTT GAA TAC AGA GTC AAC AAG AAT AAT GAC GAA ACT ACG TGC TCA ACA ATG
Ile Ser Asn Leu Glu Tyr Arg Val Asn Lys Asn Asn Asp Glu Thr Thr Cys Ser Thr Met 1770                                                    1800
TCG ATT CTG GAC ATC ATT TTT TCC AAA AGT CTT GGA AAT GAC AGG AAA TAT GAT GAA GCA
Ser Ile Leu Asp Ile Ile Phe Ser Lys Ser Leu Gly Asn Asp Arg Lys Tyr Asp Glu Ala 1830                                                    1860
GAA TGG GAG TGG AAA GCA GGA TTC CAT CGC TGG AAC AAT TAC ATG ATG GAC TGG AAA AAT
Glu Trp Glu Trp Lys Ala Gly Phe His Arg Trp Asn Asn Tyr Met Met Asp Trp Lys Asn 1890                                                    1920
CAA TTT AAC GAT TAC ACT AGC AAG AAA GAA AGT TGT GTG GGT CTC TAA TTA ATA GAT TTA
Gln Phe Asn Asp Tyr Thr Ser Lys Lys Glu Ser Cys Val Gly Leu End 1950                                                    1980
CCC TTT ATA GAA CAT ATT TTC CTT TAG ATC AAG GCA AAA ATA TCA GGA GCT TTT TTA CAC 2010                                                    2040
ACC TAC TAA AAA AGT TAT TAT GTA GCT GAA ACA CAA ATG CCA GAA GGA TAA TAT TGT TCC 2070                                                    2100
TCA CAT CTT TAA CTT AGT ATT TTA CCA TGC ATT TCA AAA CCC AAA TGG CTA GAA CAT GTT 2130                                                    2160
TAA TTA AAT TTC ACA ATA TAA AGT TCT ACA GTT AAT TAT GTG CAT ATT AAA ACA TGG CCT 2190                                                    2220
GGT TCA ATT TCT TTC TTT CCT TAA TAA ATT TAA GTT TTT TCC CCC AAA TAT CAG TGC 2250                                                    2280
TCT GCT TTT AGT CAC GTG TAT TTT CAT TAC CAC TCG TAA AAA GGT ATC TTT TTT AAA TGA 2310                                                    2340
AGT TAA ATA TTG AAA CAC TGT ACA CCA TAG TTT ACA ATA ATT AGT GTT TCC TAA GTT AAA 2370                                                    2400
ATA AGA ATT GAA TGT CAA TAA TGA GAA TAA TTA AAA TAA GCA CAG AAA ATC ACA AAA AAA

2430
AAC AAA AAA AAA AAA AAA AAA AAA AAA AAA AAA AAA AAA AAA AAA
```

EXAMPLE IX

Characterization of ChE

The FChE sequence includes the exact N-terminus, active site and c-terminus peptides published for human ψChE (Lockridge, ibid. (1984)). In Northern and Southern Gel hybridizations, it yields the same results as FBChE12. When used as a probe to screen a genomic DNA library in Charon 4A prepared with partial Hoe-3 digestion, it hybridized with five positive phages.

Clones FBChE12 and FChE currently serve for further screens of our cDNA libraries, aimed to isolate additional cholinesterase cDNA clones and determine the full amino acid sequence of other human cholinesterases. In addition, it will be used for studies of the organization, structure, and regulation of the human gene(s)

coding for cholinesterases, as well as their mRNA transcripts and protein products.

When inserted into suitable expression vectors, the above defined cDNA can direct the production of authentic human ChE with catalytic activity. The ChE thus produced can interact with OP-poisons and succinylcholine. Such ChE are highly effective as antidote against the above compounds.

Eukaryotic cells containing such constructs are suited for the large-scale production of catalytically active ChE-type products.

EXAMPLE X

Human ChE Genes Localized by Hybridization to Chromosomes 3 and 16

Using in situ chromosomal hybridization, we demonstrated that both chromosome 3 and 16 carry sequences hybridizing with ChEcDNA. One of these ChE genes localizes the structural cholinesterase-coding sequences to the $E_1$ locus at 3q21-q26, central to the transferrin gene on the longer arm of chromosome 3, and to the $E_2$ locus at a 16p11-q23 position, central to that of the haptoglobin gene on chromosome 16.

Figure 8:
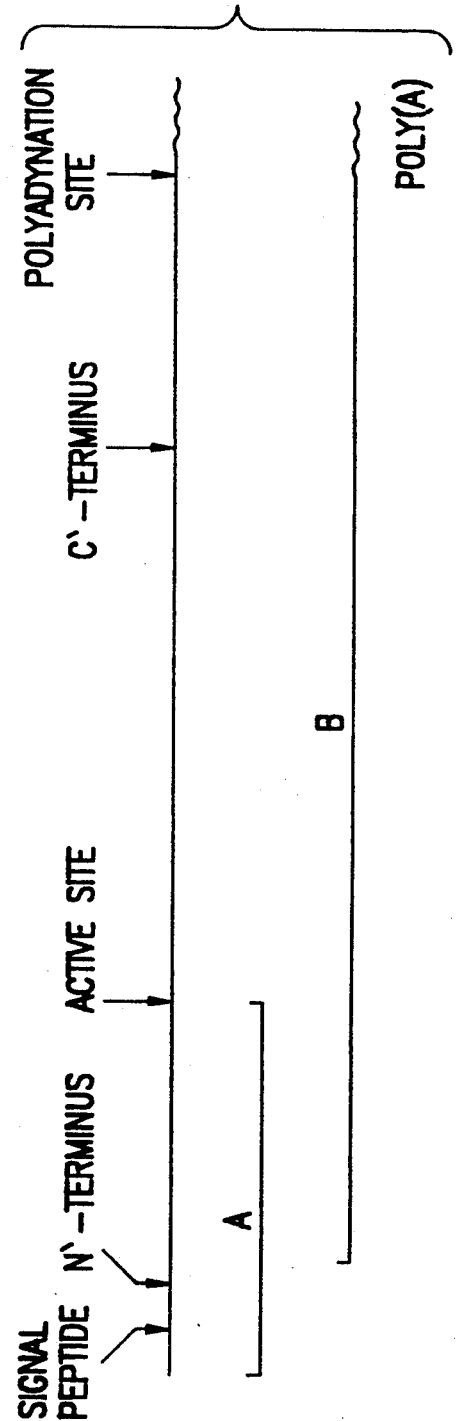
FIG. 8 shows the labeled [$^{35}$S] cDNA probe coding for approximately one-half the catalytic subunit of cholinesterase isolated from fetal human brain and the EcoRI fragment derived from a full-length cholinesterase cDNA from fetal liver origin.

In situ hybridization experiments were performed using Q-banded and R-banded chromosome preparations from peripheral blood lymphocytes and either a 760 nucleotides long [$^{35}$S]cDNA probe coding for about half of the catalytic subunit of cholinesterase isolated from fetal human brain or a 2230 nucleotides long EcoR1 fragment derived from a full-length cholinesterase cDNA from fetal liver origin (FIG. 8). Out of a total of 52 cells from eight unrelated volunteers having normal karyotypes which were scored, 53 copies of chromosome no. 3 in 43 cells and 37 copies of chromosome no. 16 in 30 cells gave positive hybridization signals. These carried 98 and 77 grains on chromosomes 3 and 16, respectively, altogether 175 grains out of a total of 646 which were associated with chromosomes, with 45 (87%) cells being positive for either one or both chromosomes. An example for R-banded chromosomes after hybridization with ChEcDNA and autoradiography is displayed in FIG. 9.

Figure 10:
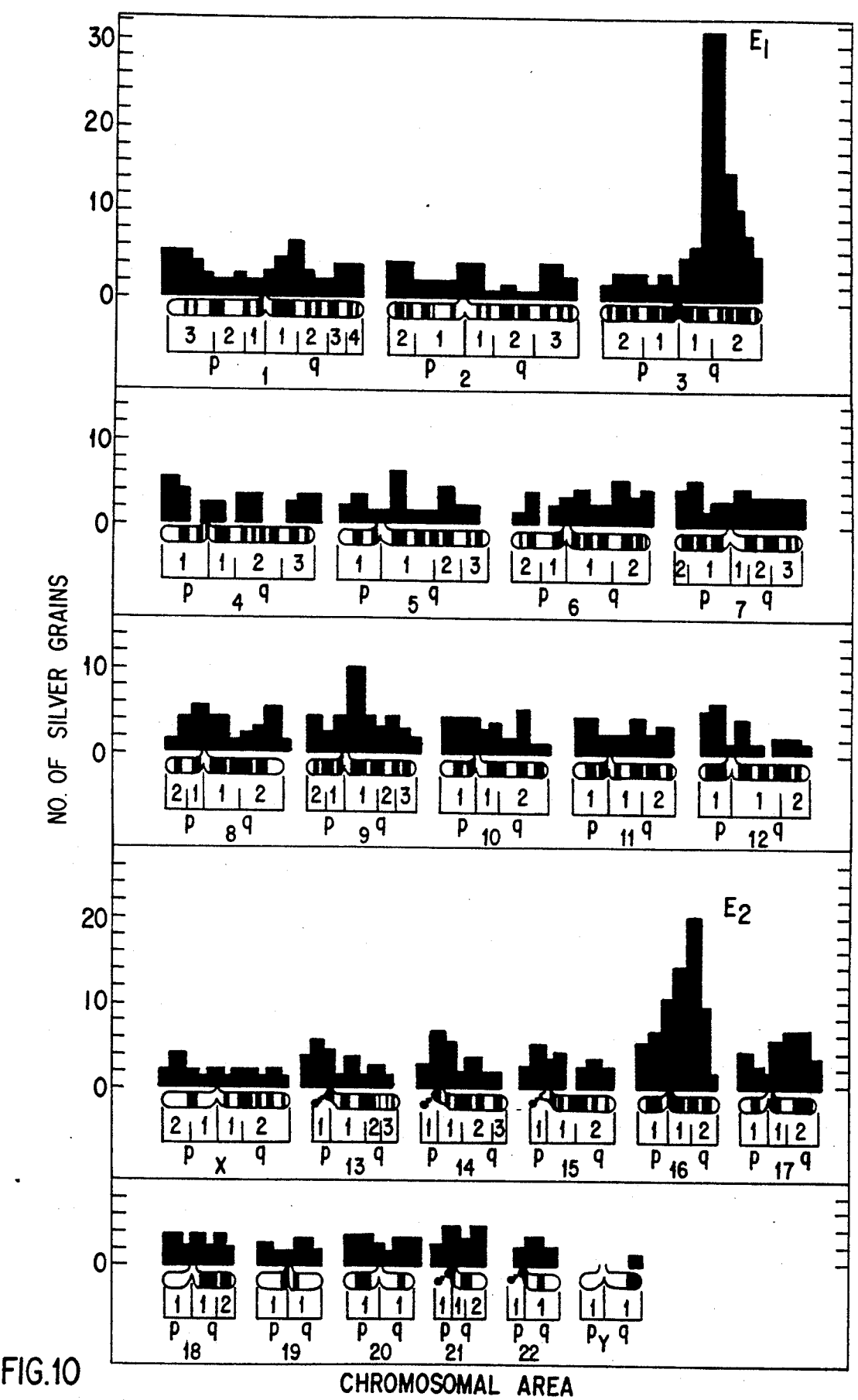
FIG. 10 is a histogram representing the haploid human genome.

The cumulative distribution of autoradiographic silver grains observed over photographed chromosome spreads were plotted on a histogram representing the haploid human genome and divided into equal units scaled to the average diameter of a silver grain (0.35 u; FIG. 10). This analysis revealed that 63 (64%) of the grains on chromosome 3 were concentrated within the region 3q21→q26, and peaked around 3q21. On the shorter chromosome 16, radioactivity concentrated around the 16q12 band, with 49 (64%) of the grains within the region 16p11→q23. Statistical evaluation of the number of silver grains per unit chromosome length, assuming a Poisson distribution, indicated that the localization on chromosome 3 and 16 was significant in both cases ($p \leq 0.025$ and $p \leq 0.01$, respectively). The labeling over all other chromosomes was not significant. The two cDNA probes gave essentially similar results, further confirming the significance of the above-mentioned hybridization experiments.

FIG. 8 shows the schematic representation of the cDNA fragments employed as probes to search for the human cholinesterase genes. The full-length human chlolinesterase mRNA (upper line), ca. 2500 nucleotides long, is expressed both in the fetal brain and liver and includes sequences coding for a signal peptide and the N-terminal, active site and C-terminal peptides (marked by arrows) found by peptide sequencing for human serum butyrylcholinesterase. Probe A represents a 760 nucleotides long cDNA insert isolated from a lambda.gt10 library of fetal brain origin and spanning from the 5'-end region of the ChEcDNA through sequence coding for the N-terminal and active site peptides of butyrylcholinesterase. Probe B represents a 2230 long cDNA fragment isolated from a lambda.gt10 library of fetal liver origin. It contains a stretch of 590 nucleotides overlapping with probe A and it spans from an EcoRl restriction site within probe A through the active site and C-terminal regions of butyrycholinesterase as well as the 3'-untranslated region and polyadenylation site of ChEcDNA.

Figure 9:
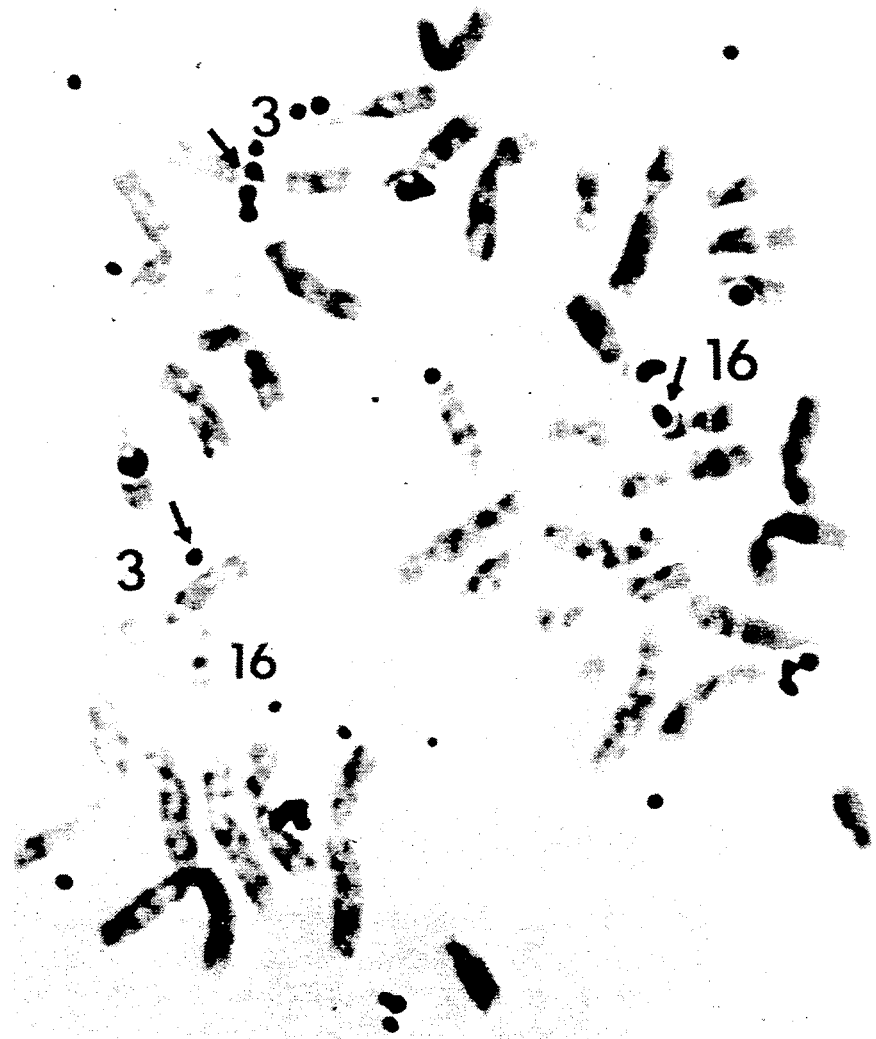
FIG. 9 shows R-banded chromosomes after hybridization with ChEcDNA and autoradiography.

FIG. 9 shows the lymphocyte metaphase chromosome spread after hybridization with [$^{35}$S]-ChEcDNA and autoradiography (exposure:12 days). Chromosome spreads from peripheral blood lymphocytes treated with 5-bromodeoxy Uracil were pre-incubated in $2 \times$SSC ($1 \times$SSC$=0.15$M NaCl and 0.015M NaCitrate), for 30 minutes at 70° C. RNA was hydrolyzed by 60 minutes incubation at 37° C. in 0.1 mg/ml of pancreatic ribonuclease (Sigma), followed by successive washes of 5 min in $2 \times$SSC and 70,80 and 100% ethanol. DNA was denatured by 4 minutes incubation at 70° C. in 70% formamide, $2 \times$SSC and 10 mM potassium phosphate buffer at a final pH of 7.0. The chromosome spreads were immediately transferred to frozen ethanol at 100, 80 and 70% concentrations for successive washes of 5 minutes and were air-dried. Each spread was then covered by a 25 ul drop of hybridization solution, containing 50% formamide, 10% dextran sulfate, $1 \times$Denhardt's solution ($1 \times$Denhardt's solution is 0.02% Ficoll, 0.02% polyvinylpirrolidone and 0.02% Bovine serum albumin) and 8 ng of the preboiled DNA probe (Probe A, FIG. 8), labeled by nicktranslation with [$^{35}$S]adenosine and [$^{35}$S]cytosine to a specific activity of $1 \times 10^8$ cpm/ug and purified by three successive precipitations in ethanol, in the presence of 10 W:W of Salmon sperm DNA as a carrier. Hybridization was for 18 hours at 37°, in a humid chamber and under cover slides. The chromosomes were then washed with 50% formamide and $2 \times$SSC (1 hr, 37° C.), $2 \times$SSC (15 minutes, 37° C.), $2 \times$SSC and 20 mM beta-mercaptoethanol (15 min, 37° C.), $2 \times$SSC (15 minutes, 37° C.), $2 \times$SSC and 20 mM beta-mercaptoethanol (15 min, 37° C.), $2 \times$SSC (15 minutes, 50° C.) and $0.15 \times$SSC (15 minutes, 50° C.), dehydrated by successive 5 minutes incubations in 70, 80 and 100% ethanol at room temperature and airdrided. Exposure was under photography emulsion (Kodak NTB-2 diluted 1:1 in $H_2O$ at 45° C.) in a dry chamber at 4° C. for 12-15 days, and development was for 0.5-1.5 minutes in D-19 Kodak developer.

Slides were then stained for 15 minutes in 150 mg/ml Hoechst 33258 Stain (Aldrich), rinsed in distilled water and dried. To create the R-bands, stained slides were mounted in $2 \times$SSC under coverslips and were illuminated for 30 minutes by a mercury vapor lamp at a distance maintaining a temperature of 47°-50° C., rinsed in distilled water and restained in 4% buffered Giemsa (Gurr-R-66) at pH 6.8. A representative partial spread, hybridized with probe A, is displayed, in which chromosomes No. 3 and 16 are marked by arrows.

FIG. 10 shows the distribution of silver grains scored over human chromosomes from 52 Q or R-banded metaphase spreads. Cumulative scores are presented from 31 and 21 metaphase spreads, respectively, hybridized with [35S]ChEcDNA probes A and B (FIG. 8). Results of experiments carried out with the two probes were essentially similar. High concentration of grains was located on the chromosome regions 3q21-q26 and 16p11-16p23, while labeling on all other chromosomes was insignificant.

Deposit in International Culture Collection

Phage FBChE12a λgt10 was deposited with the Culture Collection of Institute Pasteur, Paris, France, under Deposit No. I-534 prior to the filing date of the priority application, with instructions complying with those required for a patent application. Bacterial host strain POP2136 and plasmid FBChEpEX12a were deposited with the Culture Collection of Institute Pasteur, Paris, France, on Jul. 10, 1987, under Deposit No. I-674.

Methods for Examples

I. Brain tissues were prepared as described (Razon, N., et al., *Exp. Neurol.* 84:681–695 (1984)).
II. Preparation of polyadenylated RNA from eukaryotic tissue sources was effected as decribed (Prody, C., et al., *Neurosci. Res.* 16:25–35 (1986)).
III. Size fractionation of DNA and RNA by gel electrophoresis and sucrose gradient centrifugation was carried out as described (Soreq, H., et al., ibid., (1984); Soreq, H., et al., *Proc. Natl. Acad. Sci. USA* 82:1827–1831 (1985); Burmeister, M., et al., *EMBO Journal* 3:1499–1505 (1984)).
IV. Protein gel electrophoresis was effected by gradient polyacrylamide gel electrophoresis (5–15%) (Giveon, D., in "Molecular Biology Approach to the Neurosciences," Soreq, H., ed., *Series of Methods in Neurochemistry.* IBRO Handbook series, vol. 7, John Wiley and Sons, New York, pp. 231–243 (1984)).
V. Injection of mRNA into Xenopus oocytes was as described by Soreq, H., et al., ibid. (1982); Soreq, H., ibid. (1984), ibid. (1985).
VI. Cholinesterase radiometric assay was carried out as described by Soreq, H., et al., ibid. (1982); Soreq, H., ibid., (1984), ibid. (1985).
VII. Human genomic DNA library was generated by cloning partial Hae-3 cleavage fragments of peripheral blood DNA in Charon 4A lambda phages. (Maniatis et al., ibid. (1982), and *E. coli* K-12 bacteria were from strain LE 392 (F−, hsd R514(r−$_k$m−$_k$) supF58 LacY, gal K2, galT22, metB1, trpR55) and amplified by standard procedure (Maniatis et al., *Molecular Cloning, a Laboratory Manual:* Cold Spring Harbor Laboratory (1982)).
VIII. Digestion with restriction enzymes was performed in each case under the conditions recommended by the suppliers, New England Biolabs. The enzymatic reactions were carried out at least for 2 h at the appropriate temperature.
IX. Electroelution of DNA fragments from agarose gel, nick-translation of DNA and preparation of phage DNA (large scale) was as described (Soreq et al., ibid. (1985).
X. DNA sequencing by the Sanger dideoxy technique was according to Sanger, F., *Science* 214:1205–1210 (1981), six percent 0.2 mm thick acrylamide gels were used (Sanger et al., *FEBS Lett.* 87:107–110 (1978), Guroff et al., *Analyt. Bioch.* 115:450–457 (1981). The DNA sequences defined by the Sanger dideoxy technique were analyzed by the RUNSEQ (Sege et al., *Nuc. Acid Res.* 9:437–444 (1981) program available at the WICC.
XI. Synthesis of OPSYN oligonucleotides was carried out as described (Prody et al., ibid (1986)).
XII. Strategy for the order and synthesis and screening of OPSYN oligonucleotides. A mixture of the following 9-mer oligonucleotides was included in the 5' terminal end of all of the OPSYN preparations:

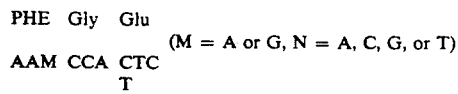

This mixture was divided into six parts, each of which was succeeded by one of the codons for serine (AGN or TOM). These were, again, divided into four mixtures each, to which we added

with N being either A, C, G, or T.
XIII. End labelling of Synthetic Oligonucleotides with [32P] ATP was according to Maniatis' handbook (1982) and as described (Prody et al., 1986).
XIV. The minimal length of the full-length FChE DNA which is necessary and sufficient for the production of catalytically active ChE in an appropriate expression system is defined by site-directed mutagenesis of expressible partial ChE cDNA clones. As set out above, a DNA expression vector comprising a DNA sequence encoding a protein having human ChE activity (AChE and/or pseudo-ChE activity) can be used for the production of such proteins. The production is first analyzed by in vitro transcription and oocyte microinjection and can be effected by means of bacterial, eukaryotic cells or yeast cells. The invention also encompasses such biologically active proteins, whenever obtained by the cultivation of such cells. Suitable systems in which catalytically active ChE of human origin can be produced in the above-described FChE cDNA sequences are thus provided. These include host systems such as bacteria, yeast, or mammalian cells in culture as well as engineered constructs, composed of appropriate expression vectors, and the entire or part of the above-described ChE cDNA sequences.
XV. Methods for the large scale production of authentic human-originated catalytically active ChE is provided, based on the use of expression systems as in XIV, transfected with constructs in which as cDNA coding for ChE has been joined end-to-end with an expression effecting DNA in an operable manner. The proteins having human AChE or human pseudo-ChE activity can be used as active ingredient in compositions having utility as prophylactics against poisoning by organphosphorus (OP) compounds, as antidotes against such OP poisoning or blocking by succinylcholine and for counteracting the effects of such OP or succinylcholine compounds. The effective doses of such active protein is in the milligram range. Such compositions can contain further active ingredients, of the type used for counteracting the effects of such OP compounds.
XVI. The minimal size of the authentic human-originated active ChE that is sufficient for protection against OP agents is provided, as defined by the synthesis of such catalytically active enzyme from human ChE cDNA shortened or modified by molecular engineering techniques, reinserted into expression vector construct and expressed in a suitable host system to yield a biologically active protein which interacts efficiently with OP agents.

XVII. The protein domain that is actively involved in OP-binding is provided as in Table I, II, III and IV. In the following, Table I defines a protein sequence that is encoded by the full-length FChE cDNA sequence and includes the complete primary sequence of human ChE, preceded by a signal peptide and an upstream peptide. Table II defines a ChE protein sequence initiating with methionine and including the signal peptide alone. Table III defines the mature ChE protein sequence, devoid of the signal and preceding peptides. Table IV defines both the nucleotide and amino acid or protein sequence for a full-length ChEcDNA.

TABLE I

|     |     |     |     |     |     |     |     |     | 10  |     |     |     |     |     |     |     |     |     | 20  |
| --- | --- | --- | --- | --- | --- | --- | --- | --- | --- | --- | --- | --- | --- | --- | --- | --- | --- | --- | --- |
| Pro | Ser | Thr | Pro | Ala | Phe | Pro | Arg | Ser | Ile | Ser | Pro | Asn | Tyr | Tyr | Met | Ile | Phe | Thr | Pro |
|     |     |     |     |     |     |     |     |     | 30  |     |     |     |     |     |     |     |     |     | 40  |
| Cys | Lys | Val | Cys | His | Leu | Cys | Cys | Arg | Glu | Ser | Glu | Ile | Asn | Met | His | Ser | Lys | Val | Thr |
|     |     |     |     |     |     |     |     |     | 50  |     |     |     |     |     |     |     |     |     | 60  |
| Ile | Ile | Cys | Ile | Arg | Phe | Leu | Phe | Trp | Phe | Val | Leu | Leu | Cys | Met | Leu | Ile | Gly | Lys | Ser |
|     |     |     |     |     |     |     |     |     | 70  |     |     |     |     |     |     |     |     |     | 80  |
| His | Thr | Glu | Asp | Asp | Ile | Ile | Ile | Ala | Thr | Lys | Asn | Gly | Lys | Val | Arg | Gly | Met | Asn | Leu |
|     |     |     |     |     |     |     |     |     | 90  |     |     |     |     |     |     |     |     |     | 100 |
| Thr | Val | Phe | Gly | Gly | Thr | Val | Thr | Ala | Phe | Leu | Gly | Ile | Pro | Tyr | Ala | Gln | Pro | Pro | Leu |
|     |     |     |     |     |     |     |     |     | 110 |     |     |     |     |     |     |     |     |     | 120 |
| Gly | Arg | Leu | Arg | Phe | Thr | Lys | Pro | Gln | Ser | Leu | Thr | Arg | Trp | Ser | Asp | Ile | Trp | Thr | Ala |
|     |     |     |     |     |     |     |     |     | 130 |     |     |     |     |     |     |     |     |     | 140 |
| Thr | Lys | Tyr | Ala | Asn | Ser | Cys | Cys | Gln | Asn | Ile | Asp | His | Ser | Phe | Pro | Gly | Phe | His | Gly |
|     |     |     |     |     |     |     |     |     | 150 |     |     |     |     |     |     |     |     |     | 160 |
| Ser | Glu | Met | Trp | Asn | Pro | Asn | Thr | Asp | Leu | Ser | Glu | Asp | Cys | Leu | Tyr | Leu | Asn | Val | Trp |
|     |     |     |     |     |     |     |     |     | 170 |     |     |     |     |     |     |     |     |     | 180 |
| Ile | Pro | Ala | Pro | Lys | Pro | Lys | Asn | Ala | Thr | Val | Leu | Ile | Trp | Ile | Tyr | Gly | Gly | Gly | Phe |
|     |     |     |     |     |     |     |     |     | 190 |     |     |     |     |     |     |     |     |     | 200 |
| Gln | Thr | Gly | Thr | Ser | Ser | Leu | His | Val | Tyr | Asp | Gly | Lys | Phe | Leu | Ala | Arg | Val | Glu | Arg |
|     |     |     |     |     |     |     |     |     | 210 |     |     |     |     |     |     |     |     |     | 220 |
| Val | Ile | Val | Val | Ser | Met | Asn | Tyr | Arg | Val | Gly | Ala | Leu | Gly | Phe | Leu | Ala | Leu | Pro | Gly |
|     |     |     |     |     |     |     |     |     | 230 |     |     |     |     |     |     |     |     |     | 240 |
| Asn | Pro | Glu | Ala | Pro | Gly | Asn | Met | Gly | Leu | Phe | Asp | Gln | Gln | Leu | Ala | Leu | Gln | Trp | Val |
|     |     |     |     |     |     |     |     |     | 250 |     |     |     |     |     |     |     |     |     | 260 |
| Gln | Lys | Asn | Ile | Ala | Ala | Phe | Gly | Gly | Asn | Pro | Lys | Ser | Val | Thr | Leu | Phe | Gly | Glu | Ser |
|     |     |     |     |     |     |     |     |     | 270 |     |     |     |     |     |     |     |     |     | 280 |
| Ala | Gly | Ala | Ala | Ser | Val | Ser | Leu | His | Leu | Leu | Ser | Pro | Gly | Ser | His | Ser | Leu | Phe | Thr |
|     |     |     |     |     |     |     |     |     | 290 |     |     |     |     |     |     |     |     |     | 300 |
| Arg | Ala | Ile | Leu | Gln | Ser | Gly | Ser | Phe | Asn | Ala | Pro | Trp | Ala | Val | Thr | Ser | Leu | Tyr | Glu |
|     |     |     |     |     |     |     |     |     | 310 |     |     |     |     |     |     |     |     |     | 320 |
| Ala | Arg | Asn | Arg | Thr | Leu | Asn | Leu | Ala | Lys | Leu | Thr | Gly | Cys | Ser | Arg | Glu | Asn | Glu | Thr |
|     |     |     |     |     |     |     |     |     | 330 |     |     |     |     |     |     |     |     |     | 340 |
| Glu | Ile | Ile | Lys | Cys | Leu | Arg | Asn | Lys | Asp | Pro | Gln | Glu | Ile | Leu | Leu | Asn | Glu | Ala | Phe |
|     |     |     |     |     |     |     |     |     | 350 |     |     |     |     |     |     |     |     |     | 360 |
| Val | Val | Pro | Tyr | Gly | Thr | Pro | Leu | Ser | Val | Asn | Phe | Gly | Pro | Thr | Val | Asp | Gly | Asp | Phe |
|     |     |     |     |     |     |     |     |     | 370 |     |     |     |     |     |     |     |     |     | 380 |
| Leu | Thr | Asp | Met | Pro | Asp | Ile | Leu | Leu | Glu | Leu | Gly | Gln | Phe | Lys | Lys | Thr | Gln | Ile | Leu |
|     |     |     |     |     |     |     |     |     | 390 |     |     |     |     |     |     |     |     |     | 400 |
| Val | Gly | Val | Asn | Lys | Asp | Glu | Gly | Thr | Ala | Phe | Leu | Val | Tyr | Gly | Ala | Pro | Gly | Phe | Ser |
|     |     |     |     |     |     |     |     |     | 410 |     |     |     |     |     |     |     |     |     | 420 |
| Lys | Asp | Asn | Ile | Ser | Ile | Ile | Thr | Arg | Lys | Glu | Phe | Gln | Glu | Gly | Leu | Lys | Ile | Phe | Phe |
|     |     |     |     |     |     |     |     |     | 430 |     |     |     |     |     |     |     |     |     | 440 |
| Pro | Gly | Val | Ser | Glu | Phe | Gly | Lys | Glu | Ser | Ile | Leu | Phe | Gln | Tyr | Thr | Asp | Trp | Val | Asp |
|     |     |     |     |     |     |     |     |     | 450 |     |     |     |     |     |     |     |     |     | 460 |
| Asp | Gln | Arg | Pro | Glu | Asn | Tyr | Arg | Glu | Ala | Leu | Gly | Cys | Met | Leu | Leu | Gly | Ile | Ile | Ile |
|     |     |     |     |     |     |     |     |     | 470 |     |     |     |     |     |     |     |     |     | 480 |
| Ser | Tyr | Ala | Leu | Pro | Phe | Glu | Val | Thr | Lys | Lys | Phe | Ser | Glu | Trp | Gly | Asn | Asn | Ala | Phe |
|     |     |     |     |     |     |     |     |     | 490 |     |     |     |     |     |     |     |     |     | 500 |
| Phe | Thr | Tyr | Phe | Glu | His | Arg | Ser | Ser | Lys | Leu | Pro | Trp | Pro | Glu | Trp | Met | Gly | Val | Met |
|     |     |     |     |     |     |     |     |     | 510 |     |     |     |     |     |     |     |     |     | 520 |
| His | Gly | Tyr | Lys | Leu | Asn | Leu | Ser | Leu | Val | Tyr | Leu | Trp | Lys | Glu | Glu | Ile | Ile | Thr | Gln |
|     |     |     |     |     |     |     |     |     | 530 |     |     |     |     |     |     |     |     |     | 540 |
| Asn | Pro | Ile | Lys | Phe | Lys | Tyr | Ile | His | Ser | Lys | Arg | Trp | Ala | Asn | Phe | Ala | Lys | Tyr | Gly |
|     |     |     |     |     |     |     |     |     | 550 |     |     |     |     |     |     |     |     |     | 560 |
| Asn | Pro | Asn | Glu | Thr | Gln | Thr | Ile | Ser | Thr | Ser | Trp | Pro | Val | Leu | Lys | Ala | Leu | Asn | Lys |
|     |     |     |     |     |     |     |     |     | 570 |     |     |     |     |     |     |     |     |     | 580 |
| Ile | Ser | Asn | Leu | Glu | Tyr | Arg | Val | Asn | Lys | Asn | Asn | Asp | Glu | Thr | Thr | Cys | Ser | Thr | Met |
|     |     |     |     |     |     |     |     |     | 590 |     |     |     |     |     |     |     |     |     | 600 |
| Ser | Ile | Leu | Asp | Ile | Ile | Phe | Ser | Lys | Ser | Leu | Gly | Asn | Asp | Arg | Lys | Tyr | Asp | Glu | Ala |
|     |     |     |     |     |     |     |     |     | 610 |     |     |     |     |     |     |     |     |     | 620 |
| Glu | Trp | Glu | Trp | Lys | Ala | Gly | Phe | His | Arg | Trp | Asn | Asn | Tyr | Met | Met | Asp | Trp | Lys | Asn |
|     |     |     |     |     |     |     |     |     | 630 |     |     |     |     |     |     |     |     |     |     |
| Gln | Phe | Asn | Asp | Tyr | Thr | Ser | Lys | Lys | Glu | Ser | Cys | Val | Gly | Leu |     |     |     |     |     |

TABLE II

|     |     |     |     |     |     |     |     |     | 10  |     |     |     |     |     |     |     |     |     | 20  |
| --- | --- | --- | --- | --- | --- | --- | --- | --- | --- | --- | --- | --- | --- | --- | --- | --- | --- | --- | --- |
| Met | His | Ser | Lys | Val | Thr | Ile | Ils | Cys | Ile | Arg | Phe | Leu | Phe | Trp | Phe | Val | Leu | Leu | Cys |
|     |     |     |     |     |     |     |     |     | 30  |     |     |     |     |     |     |     |     |     | 40  |
| Met | Leu | Ile | Gly | Lys | Ser | His | Thr | Glu | Asp | Asp | Ile | Ile | Ile | Ala | Thr | Lys | Asn | Gly | Lys |

TABLE II-continued

```
 41  Val Arg Gly Met Asn Leu Thr Val Phe Gly   50
 51  Gly Thr Val Thr Ala Phe Leu Gly Ile Pro   60
 61  Tyr Ala Gln Pro Pro Leu Gly Arg Leu Arg   70
 71  Phe Thr Lys Pro Gln Ser Leu Thr Arg Trp   80
 81  Ser Asp Ile Trp Thr Ala Thr Lys Tyr Ala   90
 91  Asn Ser Cys Cys Gln Asn Ile Asp His Ser  100
101  Phe Pro Gly Phe His Gly Ser Glu Met Trp  110
111  Asn Pro Asn Thr Asp Leu Ser Glu Asp Cys  120
121  Leu Tyr Leu Asn Val Trp Ile Pro Ala Pro  130
131  Lys Pro Lys Asn Ala Thr Val Leu Ile Trp  140
141  Ile Tyr Gly Gly Gly Phe Gln Thr Gly Thr  150
151  Ser Ser Leu His Val Tyr Asp Gly Lys Phe  160
161  Leu Ala Arg Val Glu Arg Val Ile Val Val  170
171  Ser Met Asn Tyr Arg Val Gly Ala Leu Gly  180
181  Phe Leu Ala Leu Pro Gly Asn Pro Glu Ala  190
191  Pro Gly Asn Met Gly Leu Phe Asp Gln Gln  200
201  Leu Ala Leu Gln Trp Val Gln Lys Asn Ile  210
211  Ala Ala Phe Gln Gly Asn Pro Lys Ser Val  220
221  Thr Leu Phe Gly Glu Ser Ala Gly Ala Ala  230
231  Ser Val Ser Leu His Leu Leu Ser Pro Gly  240
241  Ser His Ser Leu Phe Thr Arg Ala Ile Leu  250
251  Gln Ser Gly Ser Phe Asn Ala Pro Trp Ala  260
261  Val Thr Ser Leu Tyr Glu Ala Arg Asn Arg  270
271  Thr Leu Asn Leu Ala Lys Leu Thr Gly Cys  280
281  Ser Arg Glu Asn Glu Thr Glu Ile Ile Lys  290
291  Cys Leu Arg Asn Lys Asp Pro Gln Glu Ile  300
301  Leu Leu Asn Glu Ala Phe Val Val Pro Tyr  310
311  Gly Thr Pro Leu Ser Val Asn Phe Gly Pro  320
321  Thr Val Asp Gly Asp Phe Leu Thr Asp Met  330
331  Pro Asp Ile Leu Leu Glu Leu Gly Gln Phe  340
341  Lys Lys Thr Gln Ile Leu Val Gly Val Asn  350
351  Lys Asp Glu Gly Thr Ala Phe Leu Val Tyr  360
361  Gly Ala Pro Gly Phe Ser Lys Asp Asn Ile  370
371  Ser Ile Ile Thr Arg Lys Glu Phe Gln Glu  380
381  Gly Leu Lys Ile Phe Phe Pro Gly Val Ser  390
391  Glu Phe Gly Lys Glu Ser Ile Leu Phe Gln  400
401  Tyr Thr Asp Trp Val Asp Asp Gln Arg Pro  410
411  Glu Asp Tyr Arg Glu Ala Leu Gly Cys Met  420
421  Leu Leu Gly Ile Ile Ile Ser Tyr Ala Leu  430
431  Pro Phe Glu Val Thr Lys Lys Phe Ser Glu  440
441  Trp Gly Asn Asn Ala Phe Phe Tyr Tyr Phr  450
451  Glu His Arg Ser Ser Lys Leu Pro Trp Pro  460
461  Glu Trp Met Gly Val Met His Gly Tyr Lys  470
471  Leu Asn Leu Ser Leu Val Tyr Leu Trp Lys  480
481  Glu Glu Ile Ile Thr Gln Asn Pro Ile Lys  490
491  Phe Lys Tyr Ile His Ser Lys Arg Trp Ala  500
501  Asn Phe Ala Lys Tyr Gly Asn Pro Asn Glu  510
511  Thr Gln Thr Ile Ser Thr Ser Trp Pro Val  520
521  Leu Lys Ala Leu Asn Lys Ile Ser Asn Leu  530
531  Glu Tyr Arg Val Asn Lys Asn Asn Asp Glu  540
541  Thr Thr Cys Ser Thr Met Ser Ile Leu Asp  550
551  Ile Ile Phe Ser Lys Ser Leu Gly Asn Asp  560
561  Arg Lys Tyr Asp Glu Ala Glu Trp Glu Trp  570
571  Lys Ala Gly Phe His Arg Trp Asn Asn Tyr  580
581  Met Met Asp Trp Lys Asn Gln Phe Asn Asp  590
591  Tyr Thr Ser Lys Lys Glu Ser Cys Val Gly  600
601  Leu
```

TABLE III

```
  1  Glu Asp Asp Ile Ile Ile Ala Thr Lys Asn   10
 11  Gly Lys Val Arg Gly Met Asn Leu Thr Val   20
 21  Phe Gly Gly Thr Val Thr Ala Phe Leu Gly   30
 31  Ile Pro Tyr Ala Gln Pro Pro Leu Gly Arg   40
 41  Leu Arg Phe Thr Lys Pro Gln Ser Leu Thr   50
 51  Arg Trp Ser- Asp Ile Trp Thr Ala Thr Lys  60
 61  Tyr Ala Asn Ser Cys Cys Gln Asn Ile Asp   70
 71  His Ser Phe Pro Gly Phe His Gly Ser Glu   80
 81  Met Trp Asn Pro Asn Thr Asp Leu Ser Glu   90
 91  Asp Cys Leu Tyr Leu Asn Val Trp Ile Pro  100
101  Ala Pro Lys Pro Lys Asn Ala Thr Val Leu  110
111  Ile Trp Ile Tyr Gly Gly Gly Phe Gln Thr  120
121  Gly Thr Ser Ser Leu His Val Tyr Asp Gly  130
131  Lys Phe Leu Ala Arg Val Glu Arg Val Ile  140
141  Val Val Ser Met Asn Tyr Arg Val Gly Ala  150
151  Leu Gly Phe Leu Ala Leu Pro Gly Asn Pro  160
161  Glu Ala Pro Gly Asn Met Gly Leu Phe Asp  170
171  Gln Gln Leu Ala Leu Gln Trp Val Gln Lys  180
181  Asn Ile Ala Ala Phe Gly Gly Asn Pro Lys  190
191  Ser Val Thr Leu Phe Gly Glu Ser Ala Gly  200
201  ... ... ... ... ... ... ... ... ... ...  210
211  ... ... ... ... ... ... ... ... ... ...  220
```

TABLE III-continued

| | | | | | | | | | | | | | | | | | | |
|---|---|---|---|---|---|---|---|---|---|---|---|---|---|---|---|---|---|---|
| Ala | Ala | Ser | Val | Ser | Leu | His | Leu | Leu | Ser 230 | Pro | Gly | Ser | His | Ser | Leu | Phe | Thr | Arg | Ala 240 |
| Ile | Leu | Gln | Ser | Gly | Ser | Phe | Asn | Ala | Pro 250 | Trp | Ala | Val | Thr | Ser | Leu | Tyr | Glu | Ala | Arg 260 |
| Asn | Arg | Thr | Leu | Asn | Leu | Ala | Lys | Leu | Thr 270 | Gly | Cys | Ser | Arg | Glu | Asn | Glu | Thr | Glu | Ile 280 |
| Ile | Lys | Cys | Leu | Arg | Asn | Lys | Asp | Pro | Gln 290 | Glu | Ile | Leu | Leu | Asn | Glu | Ala | Phe | Val | Val 300 |
| Pro | Tyr | Gly | Thr | Pro | Leu | Ser | Val | Asn | Phe 310 | Gly | Pro | Thr | Val | Asp | Gly | Asp | Phe | Leu | Thr 320 |
| Asp | Met | Pro | Asp | Ile | Leu | Leu | Glu | Leu | Gly 330 | Gln | Phe | Lys | Lys | Thr | Gln | Ile | Leu | Val | Gly 340 |
| Val | Asn | Lys | Asp | Glu | Gly | Thr | Ala | Phe | Leu 350 | Val | Tyr | Gly | Ala | Pro | Gly | Phe | Ser | Lys | Asp 360 |
| Asn | Ile | Ser | Ile | Ile | Thr | Arg | Lys | Glu | Phe 370 | Gln | Glu | Gly | Leu | Lys | Ile | Phe | Phe | Pro | Gly 380 |
| Val | Ser | Glu | Phe | Gly | Lys | Glu | Ser | Ile | Leu 390 | Phe | Gln | Tyr | Thr | Asp | Trp | Val | Asp | Asp | Gln 400 |
| Arg | Pro | Glu | Asn | Tyr | Arg | Glu | Ala | Leu | Gly 410 | Cys | Met | Leu | Leu | Gly | Ile | Ile | Ile | Ser | Tyr 420 |
| Ala | Leu | Pro | Phe | Glu | Val | Thr | Lys | Lys | Phe 430 | Ser | Glu | Trp | Gly | Asn | Asn | Ala | Phe | Phe | Tyr 440 |
| Tyr | Phe | Glu | His | Arg | Ser | Ser | Lys | Leu | Pro 450 | Trp | Pro | Glu | Trp | Met | Gly | Val | Met | His | Gly 460 |
| Tyr | Lys | Leu | Asn | Leu | Ser | Leu | Val | Tyr | Leu 470 | Trp | Lys | Glu | Glu | Ile | Ile | Thr | Gln | Asn | Pro 480 |
| Ile | Lys | Phe | Lys | Tyr | Ile | His | Ser | Lys | Arg 490 | Trp | Ala | Asn | Phe | Ala | Lys | Tyr | Gly | Asn | Pro 500 |
| Asn | Glu | Thr | Gln | Thr | Ile | Ser | Thr | Ser | Trp 510 | Pro | Val | Leu | Lys | Ala | Leu | Asn | Lys | Ile | Ser 520 |
| Asn | Leu | Glu | Tyr | Arg | Val | Asn | Lys | Asn | Asn 530 | Asp | Glu | Thr | Thr | Cys | Ser | Thr | Met | Ser | Ile 540 |
| Leu | Asp | Ile | Ile | Phe | Ser | Lys | Ser | Leu | Gly 550 | Asn | Asp | Arg | Lys | Tyr | Asp | Glu | Ala | Glu | Trp 560 |
| Glu | Trp | Lys | Ala | Gly | Phe | His | Arg | Trp | Asn 570 | Asn | Tyr | Met | Met | Asp | Trp | Lys | Asn | Gln | Phe |
| Asn | Asp | Tyr | Thr | Ser | Lys | Lys | Glu | Ser | Cys | Val | Gly | Leu | | | | | | | |

TABLE IV

```
                30                                                    60
ATT TCC CCG AAC TAT TAC ATG ATT TTC ACT CCT TGC AAA GTT TGC CAT CTT TGT TGC AGA
```

```
                                90                                   120
GAA TCG AAA ATC AAT (ATG) CAT AGC AAA GTC ACA ATC ATA /TGC\ ATC AGA TTT CTC TTT TGG
                    (Met)  His  Ser  Lys Val  Thr  Ile  Ile \Cys/  Ile  Arg Phe  Leu Phe  Trp 150                                  180
TTT CTT TTG CTC /TGC\ ATG CTT ATT GGG AAG TCA CAT ACT GAA GAT GAC ATC ATA ATT GCA
Phe Leu Leu Leu \Cys/ Met Leu Ile Gly Lys Ser His Thr Glu Asp Asp Ile Ile Ile Ala 210                                                   240
ACA AAG AAT GGA AAA GTC AGA GGG ATG AAC TTG ACA GTT TTT GGT GGC ACG GTA ACA GCC
Thr Lys Asn Gly Lys Val Arg Gly Met Asn Leu Thr Val Phe Gly Gly Thr Val Thr Ala 270                                                   300
TTT CTT GGA ATT CCC TAT GCA CAG CCA CCT CTT GGT AGA CTT CGA TTC AAA AAG CCA CAG
Phe Leu Gly Ile Pro Tyr Ala Gln Pro Pro Leu Gly Arg Leu Arg Phe Lys Lys Pro Gln 330                                  360
TCT CTG ACC AAG TGG TCT GAT ATT TGG AAT GCC ACA AAA TAT GCA AAT TCT /TGC\/TGT\ CAG
Ser Leu Thr Lys Trp Ser Asp Ile Trp Asn Ala Thr Lys Tyr Ala Asn Ser \Cys/\Cys/ Gln 390                                 420
AAC ATA GAT CAA AGT TTT CCA GGC TTC (CAT) GGA TCA GAG ATG TGG AAC CCA AAC ACT GAC
Asn Ile Asp Gln Ser Phe Pro Gly Phe (His) Gly Ser Glu Met Trp Asn Pro Asn Thr Asp 450                                                      480
CTC AGT GAA GAC /TGT\ TTA TAT CTA AAT GTA TGG ATT CCA GCA CCT AAA CCA AAA AAT GCC
Leu Ser Glu Asp \Cys/ Leu Tyr Leu Asn Val Trp Ile Pro Ala Pro Lys Pro Lys Asn Ala 510                                       540
ACT GTA TTG ATA TGG ATT TAT GGT GGT GGT TTT CAA ACT GGA ACA TCA TCT TTA CAT GTT
Thr Val Leu Ile Trp Ile Tyr Gly Gly Gly Phe Gln Thr Gly Thr Ser Ser Leu His Val
```

TABLE IV-continued

```
                          570                                                                 600
TAT (GAT) GGC AAG TTT CTG GCT CGG GTT GAA AGA GTT ATT GTA GTG TCA ATG AAC TAT AGG
Tyr (Asp) Gly Lys Phe Leu Ala Arg Val Glu Arg Val Ile Val Val Ser Met Asn Tyr Arg 630                                                                 660
GTG GGT GCC CTA GGA TTC TTA GCT TGG CCA GGA AAT CCT GAG GCT CCA GGG AAC ATG GGT
Val Gly Ala Leu Gly Phe Leu Ala Leu Pro Gly Asn Pro Glu Ala Pro Gly Asn Met Gly 690                                                                 720
TTA TTT GAT CAA CAG TTG GCT CTT CAG TGG GTT CAA AAA AAT ATA GCA GCC TTT GGT GGA
Leu Phe Asp Gln Gln Leu Ala Leu Gln Trp Val Gln Lys Asn Ile Ala Ala Phe Gly Gly 750                                                                 780
AAT CCT AAA AGT GTA ACT CTC TTT GGA GAA (AGT) GCA GGA GCA GCT TCA GTT AGC CTG CAT
Asn Pro Lys Ser Val Thr Leu Phe Gly Glu (Ser) Ala Gly Ala Ala Ser Val Ser Leu His 810                                                                 840
TTG CTT TCT CCT GGA AGC CAT TCA TTG TTC ACC AGA GCC ATT CTG CAA AGT GGA TCC TTT
Leu Leu Ser Pro Gly Ser His Ser Leu Phe Thr Arg Ala Ile Leu Gln Ser Gly Ser Phe 870                                                                 900
AAT GCT CCT TGG GCG GTA ACA TCT CTT TAT GAA GCT AGG AAC AGA ACG TTG AAC TTA GCT
Asn Ala Pro Trp Ala Val Thr Ser Leu Tyr Glu Ala Arg Asn Arg Thr Leu Asn Leu Ala 930                                       960
AAA TTG ACT GGT /TGC\ TCT AGA GAG AAT GAG ACT GAA ATA ATC AAG /TGT\ CTT AGA AAT AAA
Lys Leu Thr Gly \Cys/ Ser Arg Glu Asn Glu Thr Glu Ile Ile Lys \Cys/ Leu Arg Asn Lys 990                                                                1020
GAT CCC CAA GAA ATT CTT CTG AAT GAA GCA TTT GTT GTC CCC TAT GGG ACT CCT TTG TCA
Asp Pro Gln Glu Ile Leu Leu Asn Glu Ala Phe Val Val Pro Tyr Gly Thr Pro Leu Ser 1050                                                                1080
GTA AAC TTT GGT CCG ACC GTG GAT GGT GAT TTT CTC ACT GAC ATG CCA GAC ATA TTA CTT
Val Asn Phe Gly Pro Thr Val Asp Gly Asp Phe Leu Thr Asp Met Pro Asp Ile Leu Leu 1110                                                                1140
GAA CTT GGA CAA TTT AAA AAA ACC CAG ATT TTG GTG GGT GTT AAT AAA GAT GAA GGG ACA
Glu Leu Gly Gln Phe Lys Lys Thr Gln Ile Leu Val Gly Val Asn Lys Asp Glu Gly Thr 1170                                                                1200
GCT TTT TTA GTC TAT GGT GCT CCT GGC TTC AGC AAA GAT AAC AAT AGT ATC ATA ACT AGA
Ala Phe Leu Val Tyr Gly Ala Pro Gly Phe Ser Lys Asp Asn Asn Ser Ile Ile Thr Arg 1230                                                                1260
AAA GAA TTT CAG GAA GGT TTA AAA ATA TTT TTT CCA GGA GTG AGT GAG TTT GGA AAG GAA
Lys Glu Phe Gln Glu Gly Leu Lys Ile Phe Phe Pro Gly Val Ser Glu Phe Gly Lys Glu 1290                                                                1320
TCC ATC CTT TTT CAT TAC ACA GAC TGG GTA GAT GAT CAG AGA CCT GAA AAC TAC CGT GAG
Ser Ile Leu Phe His Tyr Thr Asp Trp Val Asp Asp Gln Arg Pro Glu Asn Tyr Arg Glu 1350                                                                1380
GCC TTG GGT GAT GTT GTT GGG GAT TAT AAT TTC ATA /TGC\ CCT GCC TTG GAG TTC ACC AAG
Ala Leu Gly Asp Val Val Gly Asp Tyr Asn Phe Ile \Cys/ Pro Ala Leu Glu Phe Thr Lys 1410                                                                1440
AAG TTC TCA GAA TGG GGA AAT AAT GCC TTT TTC TAC TAT TTT GAA CAC CGA TCC TCC AAA
Lys Phe Ser Glu Trp Gly Asn Asn Ala Phe Phe Tyr Tyr Phe Glu His Arg Ser Ser Lys 1470                                                                1500
CTT CCG TGG CCA GAA TGG ATG GGA GTG ATG CAT GGC TAT GAA ATT GAA TTT GTC TTT GGT
Leu Pro Trp Pro Glu Trp Met Gly Val Met His Gly Tyr Glu Ile Glu Phe Val Phe Gly 1530                                                                1560
TTA CCT CTG GAA AGA AGA GAT AAT TAC ACA AAA GCC GAG GAA ATT TTG AGT AGA TCC ATA
Leu Pro Leu Glu Arg Arg Asp Asn Tyr Thr Lys Ala Glu Glu Ile Leu Ser Arg Ser Ile 1590                                                                1620
GTG AAA CGG TGG GCA AAT TTT GCA AAA TAT GGG AAT CCA AAT GAG ACT CAG AAC AAT AGC
Val Lys Arg Trp Ala Asn Phe Ala Lys Tyr Gly Asn Pro Asn Gly Thr Gln Asn Asn Ser 1650                                                                1680
ACA AGC TGG CCT GTC TTC AAA AGC ACT GAA CAA AAA TAT CTA ACC TTG AAT ACA GAG TCA
Thr Ser Trp Pro Val Phe Lys Ser Thr Glu Gln Lys Tyr Leu Thr Leu Asn Thr Glu Ser 1710                                                                1740
ACA AGA ATA ATG ACG AAA CTA CGT GCT CAA CAA /TGT\ CGA TTC TGG ACA TCA TTT TTT CCA
Thr Arg Ile Met Thr Lys Leu Arg Ala Gln Gln \Cys/ Arg Phe Trp Thr Ser Phe Phe Pro
```

TABLE IV-continued

```
                         1770                                                    1800
AAA GTC TTG GAA ATG ACA GGA AAT ATT GAT GAA GCA GAA TGG GAG TGG AAA GCA GGA TTC
Lys Val Leu Glu Met Thr Gly Asn Ile Asp Glu Ala Glu Trp Glu Trp Lys Ala Gly Phe 1830                                                    1860
CAT CGC TGG AAC AAT TAC ATG ATG GAC TGG AAA AAT CAA TTT AAC GAT TAC ACT AGC AAG
His Arg Trp Asn Asn Tyr Met Met Asp Trp Lys Asn Gln Phe Asn Asp Tyr Thr Ser Lys 1890                                          1920
AAA GAA AGT  TGT  GTG GGT CTC TAA TAA ATA GAT TTA CCC TTT ATA GAA CAT ATT TTC CTT
Lys Glu Ser  Cys  Val Gly Leu End 1950                                                    1980
TAG ATC AAG GCA AAA ATA TCA GGA GCT TTT TTA CAC ACC TAC TAA AAA AGT TAT TAT GTA 2010                                                    2040
GCT GAA ACA AAA ATG CCA GAA GGA TAA TAT TGA TTC CTC ACA TCT TTA ACT TAG TAT TTT 2070                                                    2100
ACC TAG CAT TTC AAA ACC CAA ATG GCT AGA ACA TGT TTA ATT AAA TTT CAC AAT ATA AAG 2130                                                    2160
TTC TAC AGT TAA TTA TGT GCA TAT TAA AAC AAT GGC CTG GTT CAA TTT CTT TCT TTC CTT 2190                                                    2220
AAT AAA TTT AAG TTT TTT CCC CCC AAA ATT ATC AGT GCT CTG CTT TTA GTC ACG TGT ATT 2250                                                    2280
TTC ATT ACC ACT CGT AAA AAG GTA TCT TTT TTA AAT GAA GTT AAA TAT TGA AAC ACT GTA 2310                                                    2340
CAC CAT AGT TTA CAA TAA TTA GTG TTT CCT AAG TTA AAA TAA GAA TTG AAT GTC AAT AAT 2370                                                    2400
GAG AAT AAT TAA AAT AAG CAC AGA AAA TCA CAA AAA AAA ACA AAA AAA AAA AAA AAA AAA
```

What is claimed is:

1. A recombinant human gene encoding a polypeptide or protein having human pseudocholinesterase enzymatic activity.

2. The recombinant gene according to claim 1, wherein said gene is selected from the group consisting of genomic DNA, cDNA, or mRNA.

3. The recombinant gene according to claim 1, wherein said gene comprises the following cDNA sequence:

```
ATT TCC CCG AAG TAT TAC ATG ATT TTC ACT CCT    33
Ile Ser Pro Lys Tyr Tyr Met Ile Phe Thr Pro

TGC AAA CTT TGC CAT CTT TGT TGC AGA GAA TCG    66
Cys Lys Leu Cys His Leu Cys Cys Arg Glu Ser

GAA ATC AAT ATG CAT AGC AAA GTC ACA ATC ATA    99
Glu Ile Asn Met His Ser Lys Val Thr Ile Ile

TGC ATC AGA TTT CTC TTT TGG TTT CTT TTG CTC    132
Cys Ile Arg Phe Leu Phe Trp Phe Leu Leu Leu

TGC ATG CTT ATT GGG AAG TCA CAT ACT GAA GAT    165
Cys Met Leu Ile Gly Lys Ser His Thr Glu Asp

GAC ATC ATA ATT GCA ACA AAG AAT GGA AAA GTC    198
Asp Ile Ile Ile Ala Thr Lys Asn Gly Lys Val

AGA GGG ATG AAC TTG ACA GTT TTT GGT GGC ACG    231
Arg Gly Met Asn Leu Thr Val Phe Gly Gly Thr

GTA ACA GCC TTT CTT GGA ATT CCC TAT GCA CAG    264
Val Thr Ala Phe Leu Gly Ile Pro Tyr Ala Gln

CCA CCT CTT GGT AGA CTT CGA TTC ACA AAG CCA    297
Pro Pro Leu Gly Arg Leu Arg Phe Thr Lys Pro

CAG TCT CTG ACC AGG TGG TCT GAT ATT TGG ACT    330
Gln Ala Thr Lys Tyr Ala Asn Ser Cys Cys Gln

GCC ACA AAA TAT GCA AAT TCT TGC TGT CAG AAC    363
Ser Leu Thr Arg Trp Ser Asp Ile Trp Thr Asn
```

-continued

```
ATA GAT CAT AGT TTT CCA GGC TTC CAT GGA TCA    396
Ile Asp His Ser Phe Pro Gly Phe His Gly Ser

GAG ATG TGG AAC CCA AAC ACT GAC CTC AGT GAA    429
Glu Met Trp Asn Pro Asn Thr Asp Leu Ser Glu

GAC TGT TTA TAT CTA AAT GTA TGG ATT CCA GCA    462
Asp Cys Leu Tyr Leu Asn Val Trp Ile Pro Ala

CCT AAA CCA AAA AAT GCC ACT GTA TTG ATA TGG    495
Pro Lys Pro Lys Asn Ala Thr Val Leu Ile Trp

ATT TAT GGT GGT GGT TTT CAA ACT GGA ACA TCA    528
Ile Tyr Gly Gly Gly Phe Gln Thr Gly Thr Ser

TCT TTA CAT GTT TAT GAT GGC AAG TTT CTG GCT    561
Ser Leu His Val Tyr Asp Gly Lys Phe Leu Ala

CGG GTT GAA AGA GTT ATT GTA GTG TCA ATG AAC    594
Arg Val Glu Arg Val Ile Val Val Ser Met Asn

TAT AGG GTG GGT GCC CTA GGA TTC TTA GCT TTG    627
Tyr Arg Val Gly Ala Leu Gly Phe Leu Ala Leu

CCA GGA AAT CCT GAG GCT CCA GGG AAC ATG GGT    660
Pro Gly Asn Pro Glu Ala Pro Gly Asn Met Gly

TTA TTT GAT CAA CAG TTG GCT CTT CAG TGG GTT    693
Leu Phe Asp Gln Gln Leu Ala Leu Gln Trp Val

CAA AAA AAT ATA GCA GCC TTT GGT GCA AAT CCT    726
Gln Lys Asn Ile Ala Ala Phe Gly Ala Asn Pro

AAA AGT GTA ACT CTC TTT GGA GAA AGT GCA GGA    759
Lys Ser Val Thr Leu Phe Gly Glu Ser Ala Gly

GCA GC                                          765
Ala Ala
```

4. The recombinant gene according to claim 1, wherein said gene comprises the following cDNA sequence:

```
                                  30                                                      60
CCG TCG ACC CCT GCA TTT CCC CGA AGT ATT TCC CCG AAC TAT TAC ATG ATT TTC ACT CCT
Pro Ser Thr Pro Ala Phe Pro Arg Ser Ile Ser Pro Asn Tyr Tyr Met Ile Phe Thr Pro 90                                            120
TGC AAA GTT TGC CAT CTT TGT TGC AGA GAA TCG GAA ATC AAT ATG CAT AGC AAA GTC ACA
Cys Lys Val Cys His Leu Cys Cys Arg Glu Ser Glu Ile Asn Met His Ser Lys Val Thr 150                                         180
ATC ATA TGC ATC AGA TTT CTC TTT TGG TTT GTT TTG CTC TGC ATG CTT ATT GGG AAG TCA
Ile Ile Cys Ile Arg Phe Leu Phe Trp Phe Val Leu Leu Cys Met Leu Ile Gly Lys Ser 210                                              240
CAT ACT GAA GAT GAC ATC ATA ATT GCA ACA AAG AAT GGA AAA GTC AGA GGG ATG AAC TTG
His Thr Glu Asp Asp Ile Ile Ile Ala Thr Lys Asn Gly Lys Val Arg Gly Met Asn Leu 270                                     300
ACA GTT TTT GGT GGC ACG GTA ACA GCC TTT CTT GGA ATT CCC TAT GCA CAG CCA CCT CTT
Thr Val Phe Gly Gly Thr Val Thr Ala Phe Leu Gly Ile Pro Tyr Ala Gln Pro Pro Leu 330                                          360
GGT AGA CTT CGA TTC ACA AAG CCA CAG TCT CTG ACC AGG TGG TCT GAT ATT TGG ACT GCC
Gly Arg Leu Arg Phe Thr Lys Pro Gln Ser Leu Thr Arg Trp Ser Asp Ile Trp Thr Ala 390                                             420
ACA AAA TAT GCA AAT TCT TGC TGT CAG AAC ATA GAT CAT AGT TTT CCA GGC TTC CAT GGA
Thr Lys Tyr Ala Asn Ser Cys Cys Gln Asn Ile Asp His Ser Phe Pro Gly Phe His Gly
```

-continued

```
                                       450                                                              480
TCA GAG ATG TGG AAC CCA AAC ACT GAC CTC AGT GAA GAC TGT  TTA TAT CTA AAT GTA TGG
Ser Glu Met Trp Asn Pro Asn Thr Asp Leu Ser Glu Asp Cys  Leu Tyr Leu Asn Val Trp 510                                                      540
ATT CCA GCA CCT AAA CCA AAA AAT GCC ACT GTA TTG ATA TGG ATT TAT GGT GGT GGT TTT
Ile Pro Ala Pro Lys Pro Lys Asn Ala Thr Val Leu Ile Trp Ile Tyr Gly Gly Gly Phe 570                                                      600
CAA ACT GGA ACA TCA TCT TTA CAT GTT TAT GAT  GGC AAG TTT CTG GCT CGG GTT GAA AGA
Gln Thr Gly Thr Ser Ser Leu His Val Tyr Asn  Gly Lys Phe Leu Ala Arg Val Glu Arg 630                                                              660
GTT ATT GTA GTG TCA ATG AAC TAT AGG GTG GGT GCC CTA GGA TTC TTA GCT TTG CCA GGA
Val Ile Val Val Ser Met Asn Tyr Arg Val Gly Ala Leu Gly Phe Leu Ala Leu Pro Gly 690                                                              720
AAT CCT GAG GCT CCA GGG AAC ATG GGT TTA TTT GAT CAA CAG TTG GCT CTT CAG TGG GTT
Asn Pro Glu Ala Pro Gly Asn Met Gly Leu Phe Asp Gln Gln Leu Ala Leu Gln Trp Val 750                                                              780
CAA AAA AAT ATA GCA GCC TTT GGT GGA AAT CCT AAA AGT GTA ACT CTC TTT GGA GAA AGT
Gln Lys Asn Ile Ala Ala Phe Gly Gly Asn Pro Lys Ser Val Thr Leu Phe Gly Glu Ser 810                                                              840
GCA GGA GCA GCT TCA GTT AGC CTG CAT TTG CTT TCT CCT GGA AGC CAT TCA TTG TTC ACC
Ala Gly Ala Ala Ser Val Ser Leu His Leu Leu Ser Pro Gly Ser His Ser Leu Phe Thr 870                                                              900
AGA GCC ATT CTG CAA AGT GGA TCC TTT AAT GCT CCT TGG GCG GTA ACA TCT CTT TAT GAA
Arg Ala Ile Leu Gln Ser Gly Ser Phe Asn Ala Pro Trp Ala Val Thr Ser Leu Tyr Glu 930                                                              960
GCT AGG AAC AGA ACG TTG AAC TTA GCT AAA TTG ACT GGT TGC TCT AGA GAG AAT GAG ACT
Ala Arg Asn Arg Thr Leu Asn Leu Ala Lys Leu Thr Gly Cys Ser Arg Glu Asn Glu Thr 990                                                             1020
GAA ATA ATC AAG TGT CTT AGA AAT AAA GAT CCC CAA GAA ATT CTT CTG AAT GAA GCA TTT
Glu Ile Ile Lys Cys Leu Arg Asn Lys Asp Pro Gln Glu Ile Leu Leu Asn Glu Ala Phe 1050                                                    1080
GTT GTC CCC TAT GGG ACT CCT TTG TCA GTA AAC TTT GGT CCG ACC GTG GAT GGT GAT TTT
Val Val Pro Tyr Gly Thr Pro Leu Ser Val Asn Phe Gly Pro Thr Val Asp Gly Asp Phe 1110                                                    1140
CTC ACT GAC ATG CCA GAC ATA TTA CTT GAA CTT GGA CAA TTT AAA AAA ACC CAG ATT TTG
Leu Thr Asp Met Pro Asp Ile Leu Leu Glu Leu Gly Gln Phe Lys Lys Thr Gln Ile Leu 1170                                                    1200
GTG GGT GTT AAT AAA GAT GAA GGG ACA GCT TTT TTA GTC TAT GGT GCT CCT GGC TTC AGC
Val Gly Val Asn Lys Asp Glu Gly Thr Ala Phe Leu Val Tyr Gly Ala Pro Gly Phe Ser 1230                                                    1260
AAA GAT AAC ATT AGT ATC ATA ACT AGA AAA GAA TTT CAA GAA GGT TTA AAA ATA TTT TTT
Lys Asp Asn Ile Ser Ile Ile Thr Arg Lys Glu Phe Gln Glu Gly Leu Lys Ile Phe Phe 1290                                                    1320
CCA GGA GTG AGT GAG TTT GGA AAG GAA TCC ATC CTT TTT CAA TAC ACA GAC TGG GTA GAT
Pro Gly Val Ser Glu Phe Gly Lys Glu Ser Ile Leu Phe Gln Tyr Thr Asp Trp Val Asp 1350                                                    1380
GAT CAA AGA CCT GAA AAC TAC CGT GAG GCC TTG GGT TGT ATG TTG TTG GGG ATT ATA ATT
Asp Gln Arg Pro Glu Asn Tyr Arg Glu Ala Leu Gly Cys Met Leu Leu Gly Ile Ile Ile 1410                                                            1410'
TCA TAT GCC CTG CCG TTT GAA GTT ACC AAG AAG TTT TCA GAA TGG GGA AAT AAT GCC TTT
Ser Tyr Ala Leu Pro Phe Glu Val Thr Lys Lys Phe Ser Glu Trp Gly Asn Asn Ala Phe 1470                                                            1500
TTC TAC TAT TTT GAA CAC CGA TCC TCC AAA CTT CCG TGG CCA GAA TGG ATG GGA GTG ATG
Phe Tyr Tyr Phe Glu His Arg Ser Ser Lys Leu Pro Trp Pro Glu Trp Met Gly Val Met
```

-continued

```
                                                       1530                                                    1560
CAT GGC TAT AAA TTG AAT TTG TCT TTG GTT TAC CTC TGG AAA GAA GAG ATA ATT ACA CAA
His Gly Tyr Lys Leu Asn Leu Ser Leu Val Tyr Leu Trp Lys Glu Glu Ile Ile Thr Gln 1590                                                      1620
AAT CCT ATT AAA TTT AAG TAC ATC CAT AGT AAA CGG TGG GCA AAT TTT GCA AAA TAT GGG
Asn Pro Ile Lys Phe Lys Tyr Ile His Ser Lys Arg Trp Ala Asn Phe Ala Lys Tyr Gly 1650                                                      1680
AAT CCA AAT GAG ACT CAG ACC ATT AGC ACA AGC TGG CCT GTC TTA AAA GCA CTG AAC AAA
Asn Pro Asn Glu Thr Gln Thr Ile Ser Thr Ser Trp Pro Val Leu Lys Ala Leu Asn Lys 1710                                              1740
ATA TCT AAC CTT GAA TAC AGA GTC AAC AAG AAT AAT GAC GAA ACT ACG TGC TCA ACA ATG
Ile Ser Asn Leu Glu Tyr Arg Val Asn Lys Asn Asn Asp Glu Thr Thr Cys Ser Thr Met 1770                                                    1800
TCG ATT CTG GAC ATC ATT TTT TCC AAA AGT CTT GGA AAT GAC AGG AAA TAT GAT GAA GCA
Ser Ile Leu Asp Ile Ile Phe Ser Lys Ser Leu Gly Asn Asp Arg Lys Tyr Asp Glu Ala 1830                                                      1860
GAA TGG GAG TGG AAA GCA GGA TTC CAT CGC TGG AAC AAT TAC ATG ATG GAC TGG AAA AAT
Glu Trp Glu Trp Lys Ala Gly Phe His Arg Trp Asn Asn Tyr Met Met Asp Trp Lys Asn 1890                                                    1920
CAA TTT AAC GAT TAC ACT AGC AAG AAA GAA AGT TGT GTG GGT CTC TAA TTA ATA GAT TTA
Gln Phe Asn Asp Tyr Thr Ser Lys Lys Glu Ser Cys Val Gly Leu End 1950                                                      1980
CCC TTT ATA GAA CAT ATT TTC CTT TAG ATC AAG GCA AAA ATA TCA GGA GCT TTT TTA CAC 2010                                                      2040
ACC TAC TAA AAA AGT TAT TAT GTA GCT GAA ACA CAA ATG CCA GAA GGA TAA TAT TGT TCC 2070                                                      2100
TCA CAT CTT TAA CTT AGT ATT TTA CCA TGC ATT TCA AAA CCC AAA TGG CTA GAA CAT GTT 2130                                                      2160
TAA TTA AAT TTC ACA ATA TAA AGT TCT ACA GTT AAT TAT GTG CAT ATT AAA ACA TGG CCT 2190                                                    2220
GGT TCA ATT TCT TTC TTT CCT TAA TAA ATT TAA GTT TTT TCC CCC CAA AAT TAT CAG TGC 2250                                                    2280
TCT GCT TTT AGT CAC GTG TAT TTT CAT TAC CAC TCG TAA AAA GGT ATC TTT TTT AAA TGA 2310                                                      2340
AGT TAA ATA TTG AAA CAC TGT ACA CCA TAG TTT ACA ATA ATT AGT GTT TCC TAA GTT AAA 2370                                                      2400
ATA AGA ATT GAA TGT CAA TAA TGA GAA TAA TTA AAA TAA GCA CAG AAA ATC ACA AAA AAA

2430
AAC AAA AAA AAA AAA AAA AAA AAA AAA AAA AAA AAA AAA AAA AAA
```

5. An expression vector comprising the gene of claim 1.

6. A host cell transformed with the expression vector of claim 5.

7. The host cell of claim 6 selected from the group consisting of culturable vertebrate, bacterial, yeast, and filaments fungi cells.

* * * * *

UNITED STATES PATENT AND TRADEMARK OFFICE
CERTIFICATE OF CORRECTION

PATENT NO. : 5,215,909  
DATED : June 1, 1993  
INVENTOR(S) : Hermona Soreq

Page 1 of 1

It is certified that error appears in the above-identified patent and that said Letters Patent is hereby corrected as shown below:

<u>Columns 37 and 38,</u>
Line 660, should read
-- GTG GGT GCC CTA GGA TTC TTA GCT TTG CCA GGA AAT CCT GAG GCT CCA GGG AAC ATG GGT
    Val Gly Ala Leu Gly Phe Leu Ala Leu Pro Gly Asn Pro Giu Ala Pro Gly Asn Met Gly --.

Line 1620, should read
-- GTG AAA CGG TGG GCA AAT TTT GCA AAA TAT GGG AAT CCA AAT GAG ACT CAG AAC AAT AGC
    Val Lys Arg Trp Ala Asn Phe Ala Lys Tyr Gly Asn Pro <u>Asn Glu Thr</u> Gln Asn <u>Asn Ser</u> --.

Signed and Sealed this

Second Day of May, 2006

JON W. DUDAS  
*Director of the United States Patent and Trademark Office*